US012655379B2

(12) United States Patent　　　　(10) Patent No.:　US 12,655,379 B2

Matsunaga et al.　　　　　　　　　(45) Date of Patent:　　Jun. 16, 2026

(54) DEVICE FOR EVALUATION OF CHEMICAL SUBSTANCE AND METHOD FOR EVALUATION OF CHEMICAL SUBSTANCE

(71) Applicants: SHINKO CHEMICAL CO., LTD., Kanazawa (JP); Public University Corporation Nagoya City University, Nagoya (JP)

(72) Inventors: Tamihide Matsunaga, Nagoya (JP); Takahiro Iwao, Nagoya (JP); Satoshi Kondo, Nagoya (JP); Atsushi Doi, Kanazawa (JP); Isao Saito, Kanazawa (JP)

(73) Assignees: SHINKO CHEMICAL CO., LTD., Ishikawa (JP); PUBLIC UNIVERSITY CORPORATION NAGOYA CITY UNIVERSITY, Aichi (JP)

( * ) Notice: Subject to any disclaimer, the term of this patent is extended or adjusted under 35 U.S.C. 154(b) by 1049 days.

(21) Appl. No.: 16/514,762

(22) PCT Filed: Jan. 18, 2018

(86) PCT No.: PCT/JP2018/001356
§ 371 (c)(1),
(2) Date: Jul. 17, 2019

(87) PCT Pub. No.: WO2018/135572
PCT Pub. Date: Jul. 26, 2018

(65) Prior Publication Data
US 2020/0040294 A1　　Feb. 6, 2020

(30) Foreign Application Priority Data

Jan. 18, 2017　　(JP) ................................. 2017-006873

(51) Int. Cl.
*C12M 1/00*　　　(2006.01)
*C12M 1/02*　　　(2006.01)
　　　　　　(Continued)

(52) U.S. Cl.
CPC ............ *C12M 23/34* (2013.01); *C12M 23/22* (2013.01); *C12M 23/38* (2013.01); *C12M 25/00* (2013.01);
　　　　　　(Continued)

(58) Field of Classification Search
CPC .............................. C12M 23/34; C12M 25/04
See application file for complete search history.

(56) References Cited

U.S. PATENT DOCUMENTS 5,580,790 A * 12/1996 Wall ...................... G01N 21/07
　　　　　　　　　　　　　　　　　422/562
6,475,777 B1 11/2002 Sarem et al.
　　　　　　　(Continued)

FOREIGN PATENT DOCUMENTS

CN　　　102676369 A　　9/2012
CN　　　104743752 A　　7/2015
　　　　　　(Continued)

OTHER PUBLICATIONS

Horton ("Weir Experiments, Coefficients, and Formulas"). 1907. (Year: 1907).*
　　　　　　(Continued)

*Primary Examiner* — Michael A Marcheschi
*Assistant Examiner* — Nathan G Esperon
(74) *Attorney, Agent, or Firm* — Crowell & Moring LLP

(57)　　　　　ABSTRACT

There are provided a device and a method for more appropriate evaluation of a chemical substance. The device for the evaluation of the chemical substance includes a first com-
　　　　　　(Continued)

partment, a second compartment that communicates with the first compartment and is separated from the first compartment by a partition wall.

15 Claims, 28 Drawing Sheets

(51) Int. Cl.
C12M 1/12 (2006.01)
G01N 33/50 (2006.01)

(52) U.S. Cl.
CPC ............ C12M 27/00 (2013.01); C12M 29/10 (2013.01); G01N 33/5008 (2013.01); G01N 33/5014 (2013.01)

(56) References Cited

U.S. PATENT DOCUMENTS

| | | | | |
|---|---|---|---|---|
| 8,501,462 | B2 * | 8/2013 | Eddington | ............. C12M 23/34 |
| | | | | 435/297.2 |
| 8,617,879 | B2 | 12/2013 | Yu et al. | |
| 9,617,521 | B2 * | 4/2017 | Wamhoff | ............. C12N 5/0697 |
| 10,876,088 | B2 * | 12/2020 | Griffith | .................. C12M 23/12 |
| 2003/0082632 | A1 * | 5/2003 | Shumate | ............. G01N 33/537 |
| | | | | 435/7.1 |
| 2003/0082795 | A1 | 5/2003 | Shuler et al. | |
| 2005/0101010 | A1 * | 5/2005 | Li | .......................... C12M 23/12 |
| | | | | 435/304.3 |
| 2005/0260745 | A1 * | 11/2005 | Domansky | .......... B01L 3/50255 |
| | | | | 435/294.1 |
| 2007/0059818 | A1 * | 3/2007 | Yabuki | ................... C12M 25/06 |
| | | | | 435/297.5 |
| 2007/0166816 | A1 * | 7/2007 | Campbell | ............. C12M 25/02 |
| | | | | 435/288.5 |
| 2010/0273258 | A1 * | 10/2010 | Lannutti | ................ C12M 35/04 |
| | | | | 435/366 |
| 2012/0065047 | A1 * | 3/2012 | Chapman | ............. B04B 5/0414 |
| | | | | 422/548 |
| 2014/0196550 | A1 * | 7/2014 | Chernomorsky | ...... C12M 23/12 |
| | | | | 73/864.91 |
| 2015/0247112 | A1 * | 9/2015 | Orr | ......................... C12M 29/10 |
| | | | | 435/395 |
| 2017/0197216 | A1 | 7/2017 | Tsujimaru | |

| | | | | |
|---|---|---|---|---|
| 2017/0227525 | A1 * | 8/2017 | Griffith | ................... F04B 43/12 |
| 2017/0307594 | A1 * | 10/2017 | Lyer | .................... B01L 3/50273 |
| 2019/0076840 | A1 * | 3/2019 | Gottardi | ................ C12M 41/36 |
| 2020/0263118 | A1 * | 8/2020 | Hajipouran Benam | ..................... C12M 25/02 |

FOREIGN PATENT DOCUMENTS

| | | | | | |
|---|---|---|---|---|---|
| CN | 105567564 | A | | 5/2016 | |
| CN | 105624039 | A | | 6/2016 | |
| EP | 2955220 | A1 | | 12/2015 | |
| JP | 2003-210157 | A | | 7/2003 | |
| JP | 2004-129558 | A | | 4/2004 | |
| JP | 2005-503169 | A | | 2/2005 | |
| JP | 2007-510429 | A | | 4/2007 | |
| JP | 2014-233275 | A | | 12/2014 | |
| JP | 2014233275 | | * | 12/2014 | |
| WO | WO93/11498 | A1 | | 6/1993 | |
| WO | WO 94/28501 | | | 12/1994 | |
| WO | WO 2010-110754 | A1 | | 9/2010 | |
| WO | WO2013/086509 | A1 | | 6/2013 | |
| WO | WO-2015142462 | A1 | * | 9/2015 | ........... C12M 21/08 |
| WO | WO 2016/069885 | A1 | | 5/2016 | |
| WO | WO 2016-121886 | A1 | | 8/2016 | |

OTHER PUBLICATIONS

Merriam-Webster Online Dictionary. "Increment" https://www.merriam-webster.com/dictionary/increment Retrieved Jun. 14, 2024. (Year: 2024).*

Merriam-Webster Online Dictionary. "Incremental" Retrieved Jun. 14, 2024. https://www.merriam-webster.com/dictionary/incrementally (Year: 2024).*

Office Action in Japan Application No. 2018-562427, dated Sep. 27, 2022, 13 pages, including English translation.

EESR of EP18742157.3 issued on Oct. 20, 2020, 8 pages.

Aoe, Seiichiro, "Effects of Dietary Fiber on the Function of the Upper Gastrointestinal Tract," Journal of Japanese Association for Dietary Fiber Research), non-official translation ("1. Introduction", "6. Summary") 2006, vol. 10, No. 2, pp. 53-63, pp. 53, 54.

ISR of PCT/JP2018/001356, dated Apr. 10, 2018, 2 pages.

English Translation of CN104743752 dated Jul. 1, 2015 (14 pages).

Chinese language Office Action issued in Chinese Application No. 201880007139.5 dated Jul. 29, 2022, with English translation (14 pages).

* cited by examiner

Fig. 14B

ORGAN (INTESTINAL TRACT AND LIVER)-MODEL: HEPATITIS MODEL BY HUMAN HEPATITIS B VIRUS

Figure 15B:
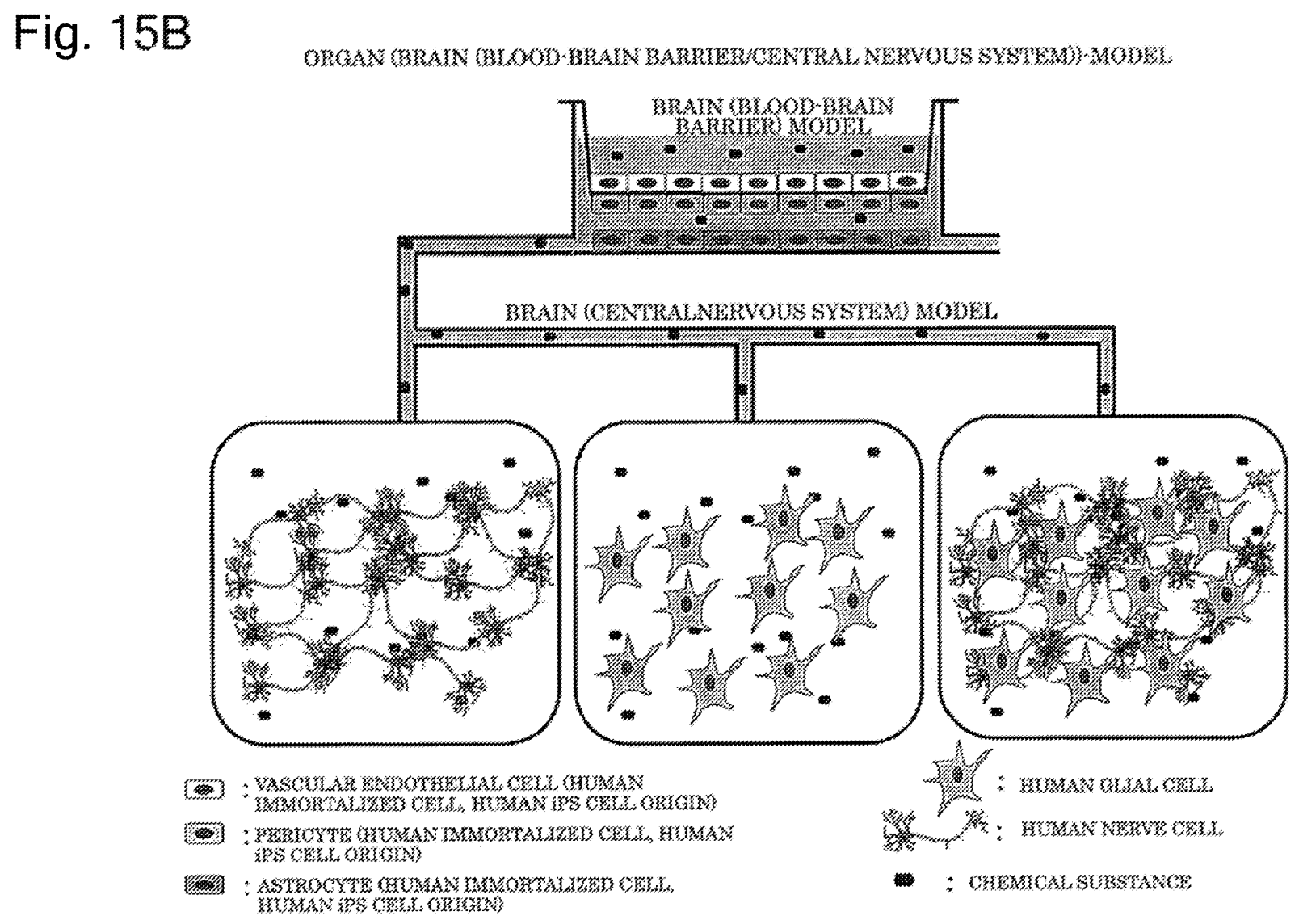

ORGAN (BRAIN (BLOOD-BRAIN BARRIER/CENTRAL NERVOUS SYSTEM)) MODEL

BRAIN (BLOOD-BRAIN BARRIER) MODEL

BRAIN (CENTRAL NERVOUS SYSTEM) MODEL

: HUMAN GLIAL CELL

: HUMAN NERVE CELL

: CHEMICAL SUBSTANCE

: VASCULAR ENDOTHELIAL CELL (HUMAN IMMORTALIZED CELL, HUMAN IPS CELL ORIGIN)

: PERICYTE (HUMAN IMMORTALIZED CELL, HUMAN IPS CELL ORIGIN)

: ASTROCYTE (HUMAN IMMORTALIZED CELL, HUMAN IPS CELL ORIGIN)

Fig. 17

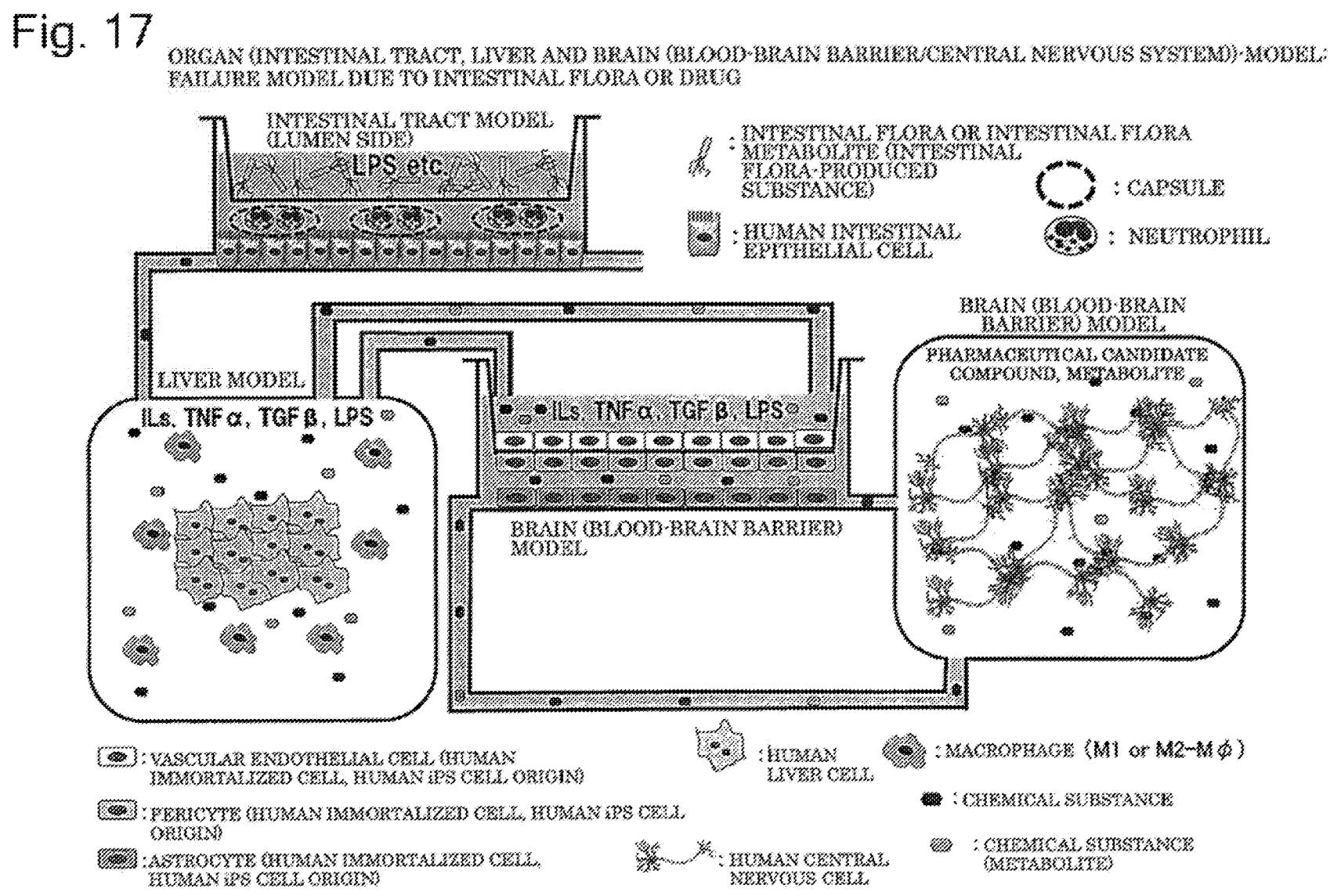

ORGAN (INTESTINAL TRACT, LIVER AND BRAIN (BLOOD-BRAIN BARRIER/CENTRAL NERVOUS SYSTEM)) MODEL: FAILURE MODEL DUE TO INTESTINAL FLORA OR DRUG

INTESTINAL TRACT MODEL (LUMEN SIDE)

LPS, etc.

LIVER MODEL

IL8, TNF α, TGF β, LPS

BRAIN (BLOOD-BRAIN BARRIER) MODEL

IL8, TNF α, TGF β, LPS

BRAIN (BLOOD-BRAIN BARRIER) MODEL

PHARMACEUTICAL CANDIDATE COMPOUND, METABOLITE

: CAPSULE

: NEUTROPHIL

: INTESTINAL FLORA OR INTESTINAL FLORA METABOLITE (INTESTINAL FLORA-PRODUCED SUBSTANCE)

: HUMAN INTESTINAL EPITHELIAL CELL

: MACROPHAGE (M1 or M2-M φ)

: CHEMICAL SUBSTANCE

: CHEMICAL SUBSTANCE (METABOLITE)

: HUMAN LIVER CELL

: HUMAN CENTRAL NERVOUS CELL

: VASCULAR ENDOTHELIAL CELL (HUMAN IMMORTALIZED CELL, HUMAN iPS CELL ORIGIN)

: PERICYTE (HUMAN IMMORTALIZED CELL, HUMAN iPS CELL ORIGIN)

: ASTROCYTE (HUMAN IMMORTALIZED CELL, HUMAN iPS CELL ORIGIN)

Fig. 19
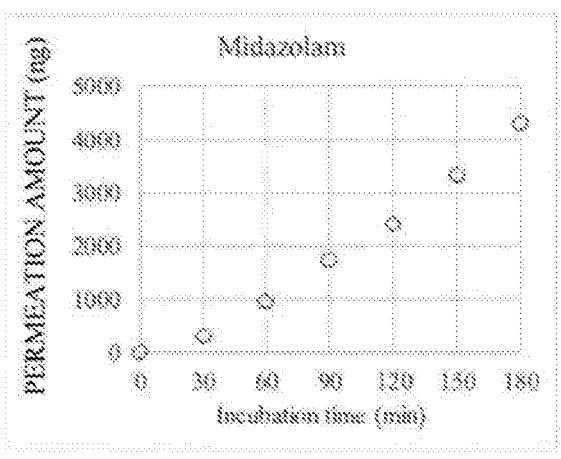
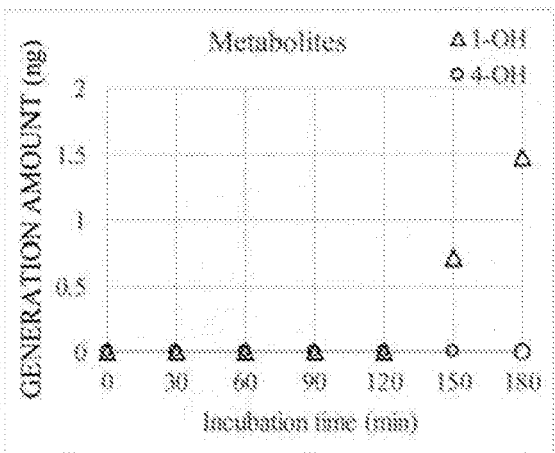
Fig. 20
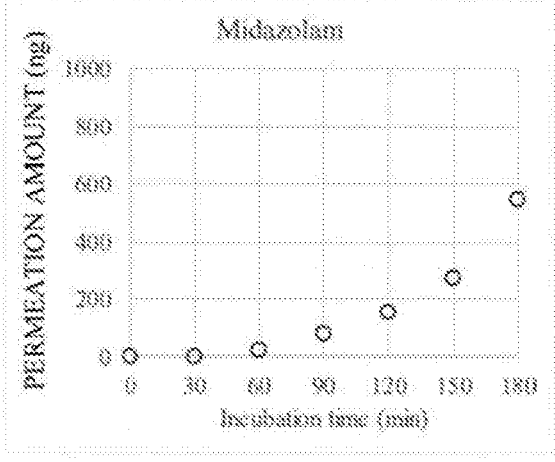
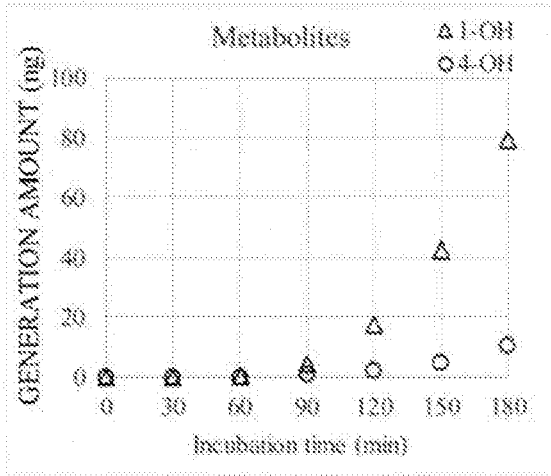

DEVICE FOR EVALUATION OF CHEMICAL SUBSTANCE AND METHOD FOR EVALUATION OF CHEMICAL SUBSTANCE

This application is a 371 application of PCT/JP2018/001356 having an international filing date of Jan. 18, 2018, which claims priority to JP2017-006873 filed Jan. 18, 2017, the entire content of each of which is incorporated herein by reference.

TECHNICAL FIELD

The present invention relates to a device for evaluation of a chemical substance and a method for the evaluation of the chemical substance.

BACKGROUND ART

Pharmaceuticals have various dosage forms, and an administration route of the pharmaceuticals is wide ranging, but an oral preparation is a dosage form most frequently used in clinical practice. An orally administered chemical substance is absorbed mainly by a small intestine and passes into general circulatory system through the portal vein and the liver. Consequently, the oral preparation undergoes first pass effects (absorption, metabolism and excretion) in the small intestine and liver, and thus decrease in bioavailability and inter-individual variations thereof are important problems in a chemical substance therapy. Therefore, when development candidate substances are prioritized and chemical substance dynamics in humans are predicted, it is important to accurately predict the first pass effects in an intestinal tract and the liver. Known devices capable of evaluating such chemical substance dynamics include cell culture devices described in the following patent literatures 1 and 2.

CITATION LIST

Patent Literature

PTL 1: National Publication of International Patent Application No. 2005-503169
PTL 2: International Publication No. WO 94/28501

SUMMARY OF INVENTION

Technical Problem

However, in devices of the above patent literatures 1 and 2, first pass effects in a small intestine and a liver cannot be simultaneously evaluated, and metabolic stability and absorbency of a chemical substance are separately evaluated in an in vitro experiment. Furthermore, in an in vivo experiment in which an experiment animal is used, indirect evaluations by PS method and the like are performed. For example, a degree and a rate of absorption in the small intestine, and a passage rate in a liver are evaluated from a difference between a concentration of the chemical substance in blood of a portal vein and a concentration of the chemical substance in blood of a whole body circulatory system after administration of the chemical substance. However, these methods have a problem of a dynamic type difference of the chemical substance and an ethical problem. Such problems are not limited to the evaluation of in vivo pharmacokinetics such as the first pass effects of the chemical substance in the small intestine and liver, and the problems are also common in evaluation of an influence of the chemical substance passing through a plurality of tissues and organs of a living body on the living body (e.g., evaluation of a medicinal effect or a pharmacological effect, or evaluation of a toxicity).

In consequence, there are desired a device and a method for more appropriate evaluation of a chemical substance.

Solution to Problem

The present invention has been developed to solve at least parts of the above described problems, and can be achieved, for example, as the following aspects.

According to a first aspect of the present invention, there is provided a device for evaluation of a chemical substance. This device includes a first compartment, and a second compartment that communicates with the first compartment and is separated from the first compartment by a partition wall.

According to this device for the evaluation of the chemical substance, the chemical substance passing through a plurality of tissues and organs of a living body can be suitably evaluated. For example, this device can be used as follows. First, cultured cells are disposed in the first compartment and the second compartment. Next, a perfusion fluid is continuously injected into the first compartment. This perfusion fluid flows through the first compartment, flows over the partition wall into the second compartment, and is discharged from the second compartment. In a state where the perfusion fluid flows in this manner, the chemical substance of an evaluation object is thrown into the first compartment. Then, the cells disposed in the respective compartments are observed, and the perfusion fluid in the first compartment and the perfusion fluid discharged from the second compartment are sampled to measure predetermined items. Consequently, the cells in the first compartment and the cells in the second compartment are simultaneously evaluated. That is, the cells in the first compartment and the cells in the second compartment can be associated with each other and evaluated under an environment that imitates a body of an animal (including a human in the present application). In addition to the first and second compartments, an additional compartment may be provided.

According to a second aspect of the present invention, in the first aspect, the device includes a cover that covers the first compartment and the second compartment. According to such an aspect, the cover is mounted to the first compartment and the second compartment during an evaluation test, so that a test environment can be easily kept in a clean state.

According to a third aspect of the present invention, in the second aspect, in the cover, a sampling hole extending through the cover and opening in at least one of the first compartment and the second compartment is formed. According to such an aspect, in a state where the cover is mounted to the first compartment and the second compartment, the perfusion fluid flowing through the first compartment and the second compartment can be easily sampled via the sampling hole.

According to a fourth aspect of the present invention, in the second or third aspect, in the cover, a chemical substance throw port extending through the cover to throw the chemical substance into the first compartment is formed. According to this aspect, in the state where the cover is mounted to the first compartment and the second compartment, the chemical substance of the evaluation object can be easily thrown via the chemical substance throw port.

According to a fifth aspect of the present invention, in any one of the second to fourth aspects, in the cover, an inlet port that communicates with the first compartment to inject a perfusion fluid into the first compartment is formed. According to the aspect, in the state where the cover is mounted to the first compartment and the second compartment, the perfusion fluid can be easily injected into the first compartment via the inlet.

According to a sixth aspect of the present invention, in any one of the second to fifth aspects, in a wall portion that forms the first compartment, a support structure is formed to support a cell culture container in which cells are to be cultured, in a state where the cell culture container is inserted in the first compartment. According to such an aspect, the cell culture container can be inserted in the first compartment. That is, while culturing, in the second compartment, the cells disposed in the second compartment, the cells to be disposed in the first compartment are cultured in another location under another condition, and can be then disposed in the first compartment. Alternatively, when the cells are cultured also in a bottom portion of the first compartment, the cells and the cells to be cultured in the cell culture container can be cultured on separate conditions.

According to a seventh aspect of the present invention, in the sixth aspect including the fifth aspect, the inlet port is formed to communicate with a region outside the cell culture container in the first compartment, in a state where the cell culture container is supported by the support structure. According to such an aspect, a transwell can be used as the cell culture container. That is, in a state where the perfusion fluid flows outside the transwell, the chemical substance can be thrown into the transwell, and evaluated under an environment where the chemical substance passed through a film of the transwell flows into the perfusion fluid (e.g., a model that imitates a small intestine corresponds).

According to an eighth aspect of the present invention, in any one of the second to seventh aspects, the cover is formed of a transparent member. According to such an aspect, the cells in the first compartment and the second compartment can be observed by using a microscope.

According to a ninth aspect of the present invention, in any one of the first to eighth aspects, a bottom portion of each of the first compartment and the second compartment is formed of a transparent member. According to such an aspect, the cells in the first compartment and the second compartment can be observed by using the microscope.

According to a tenth aspect of the present invention, in any one of the first to ninth aspects, the partition wall has, in the first compartment, an inclined surface inclined so that a wall height increases toward the second compartment. According to such an aspect, flow of the perfusion fluid flowing from the first compartment over the partition wall into the second compartment can be slowed down. As a result, it is possible to suppress concentration change of the chemical substance in the perfusion fluid due to rapid fluctuation of the flow of the perfusion fluid.

According to an eleventh aspect of the present invention, in the tenth aspect, in the inclined surface, a groove extending from a top of the inclined surface toward a surface side of the first compartment is formed. According to such an aspect, capillary phenomenon moves the perfusion fluid from the first compartment to the second compartment through the groove little by little. Therefore, pulsation flow is inhibited from being generated when the perfusion fluid flows over the partition wall. As a result, it is possible to suppress the concentration change of the chemical substance in the perfusion fluid due to the pulsating flow of the perfusion fluid.

According to a twelfth aspect of the present invention, any one of the first to eleventh aspects includes a circulation inlet port and a circulation outlet port that connect to a pump to circulate the perfusion fluid through a route extending through the second compartment. According to such an aspect, the perfusion fluid can be circulated via the inlet port and the outlet port. Therefore, it is possible to evaluate a long term influence of the chemical substance under an environment that imitates a circulatory system of the animal.

According to a thirteenth aspect of the present invention, in any one of the first to twelfth aspects, the second compartment is disposed around the first compartment to at least partially surround the first compartment. According to such an aspect, the first and second compartments can be compactly arranged, and longitudinal and lateral widths of the device can be decreased.

According to a fourteenth aspect of the present invention, in any one of the first to twelfth aspects, the second compartment is disposed side by side with the first compartment. According to such an aspect, one of the longitudinal and lateral widths of the device can be decreased. Therefore, when a plurality of devices are arranged side by side for use, the plurality of devices are arranged in a lateral direction. Consequently, the plurality of devices can be compactly arranged, and longitudinal and lateral widths of all the plurality of devices can be decreased.

According to a fifteenth aspect of the present invention, in any one of the first to fourteenth aspects, the second compartment includes a discharge port, and the discharge port includes a V-shaped inner bottom surface. According to such an aspect, a discharge region of the perfusion fluid to be discharged from the discharge port can be limited.

According to a sixteenth aspect of the present invention, in the fifteenth aspect, the discharge port includes an outer edge portion on a downstream side, and an outer bottom surface of the discharge port projects from the outer edge portion. According to such an aspect, the perfusion fluid discharged from the discharge port can be inhibited from entering a second compartment side along the outer bottom surface.

According to a seventeenth aspect of the present invention, a kit for evaluation of a chemical substance is provided. This kit includes the device according to any one of the first to sixteenth aspects. The device includes a plurality of devices. Each of the plurality of devices includes a base. Each base includes an engagement structure in which adjoining bases are engageable with each other when the plurality of devices are arranged side by side. According to such an aspect, the plurality of devices can be easily fixedly arranged side by side.

According to an eighteenth aspect of the present invention, there is provided a kit for evaluation of a chemical substance. This kit includes the device according to any one of the first to sixteenth aspects. This device includes a plurality of devices. The kit further includes a case that stores the plurality of devices in a state where the plurality of devices are arranged side by side. According to such an aspect, the plurality of devices can be easily fixedly arranged side by side. A region of the case which corresponds to a position of a bottom portion of each compartment of the device may be opened, or a bottom portion of the case may be formed of a transparent member.

According to a nineteenth aspect of the present invention, there is provided a device for evaluation of a chemical substance. This device includes N (N is an integer of 3 or more) compartments that communicate in series, and N−1 partition walls that separate two adjoining compartments among the N compartments. Such an aspect produces an effect similar to the effect of the first aspect. Any one of the second to eighteenth aspects may be added to the nineteenth aspect.

According to a twentieth aspect of the present invention, there is provided a device for evaluation of a chemical substance. This device includes N (N is an integer of 2 or more) compartments that communicate in series, and N−1 partition walls that separate two adjoining compartments among the N compartments. In a wall portion that forms each of the N compartments, a support structure is formed to support a cell culture container in which cells are to be cultured, in a state where the cell culture container is inserted in each of the N compartments. According to such a device, the cell culture containers are inserted in an arbitrary number of compartments at arbitrary positions among the N compartments, and a desired evaluation object environment can be modeled. Furthermore, the evaluation object environment can be easily changed by changing an insertion position of the cell culture container, so that the device has an excellent versatility.

According to a twenty-first aspect of the present invention, in the first aspect, the first compartment includes N (N is an integer of 2 or more) first compartments. The partition wall includes N partition walls. The second compartment includes N second compartments that communicate with the N first compartments, respectively, in a one-to-one correspondence, the N second compartments being separated from the N first compartments by the N partition walls, respectively. According to such an aspect, in a single device, a plurality of pairs of the first compartment and the second compartment can be acquired.

According to a twenty-second aspect of the present invention, the twenty-first aspect includes a cover that covers the N first compartments and the N second compartments. The cover includes N sampling holes each of which opens in at least one of each of the N first compartments and each of the N second compartments, N chemical substance throw ports to throw the chemical substance into the N first compartments, respectively, N inlet ports that communicate with the N first compartments, respectively, to inject a perfusion fluid into the N first compartments, and N outlet ports that communicate with the N second compartments, respectively, to discharge the perfusion fluid from the N second compartments. According to such an aspect, when a tube is inserted in each of the sampling hole, the chemical substance throw port, the inlet port and the outlet port, circulation of the perfusion fluid, throwing of the chemical substance and sampling of the perfusion fluid can be automatically performed.

According to a twenty-third aspect of the present invention, there is provided a method for evaluation of a chemical substance. This method includes disseminating cells in the respective compartments of the device according to any one of the first to sixteenth aspects and the nineteenth to twenty-second aspects, applying the chemical substance to any one of the compartments, and evaluating the chemical substance in each compartment.

According to a twenty-fourth aspect of the present invention, in the twenty-third aspect, the evaluation of the chemical substance is evaluation of in vivo pharmacokinetics of the chemical substance, evaluation of an effect or evaluation of a toxicity.

According to a twenty-fifth aspect of the present invention, in the twenty-third or twenty-fourth aspect, the method for the evaluation of the chemical substance includes disseminating different cells in the respective compartments.

According to a twenty-sixth aspect of the present invention, in any one of the twenty-third to twenty-fifth aspects, the method for the evaluation of the chemical substance includes applying different chemical substances to a single compartment or a plurality of compartments.

According to a twenty-seventh aspect of the present invention, in any one of the twenty-third to twenty-sixth aspects, the method for the evaluation of the chemical substance includes adding dietary fibers to a liquid in the compartment, and stirring the liquid to which the dietary fibers are added in the compartment.

A twenty-eighth aspect of the present invention includes an organ model in which cells of one or more organs are applied to the device of any one of the first to sixteenth aspects and the nineteenth to twenty-second aspects.

A twenty-ninth aspect of the present invention includes use of the device of any one of the first to sixteenth aspects and the nineteenth to twenty-second aspects, or the organ model of the twenty-eighth aspect in the method of any one of the twenty-third to twenty-seventh aspects.

BRIEF DESCRIPTION OF DRAWINGS

FIG. 14B is another example of the organ (the intestinal tract and liver)-model (the hepatitis model by the human hepatitis B virus).

FIG. 15A is an example of an organ (a brain (a blood-brain barrier/central nervous system))-model.

FIG. 15B is another example of the organ (the brain (the blood-brain barrier/central nervous system))-model.

FIG. 17 is another example of the organ (the intestinal tract, liver and brain (the blood-brain barrier/central nervous system))-model, and an example of a failure model due to intestinal flora or drug.

FIG. 19 shows a permeation amount of midazolam and an amount of a metabolite to be generated in a small intestine compartment.

FIG. 20 shows a permeation amount of midazolam and an amount of a metabolite to be generated in a liver compartment.

DESCRIPTION OF EMBODIMENTS

Figure 1:
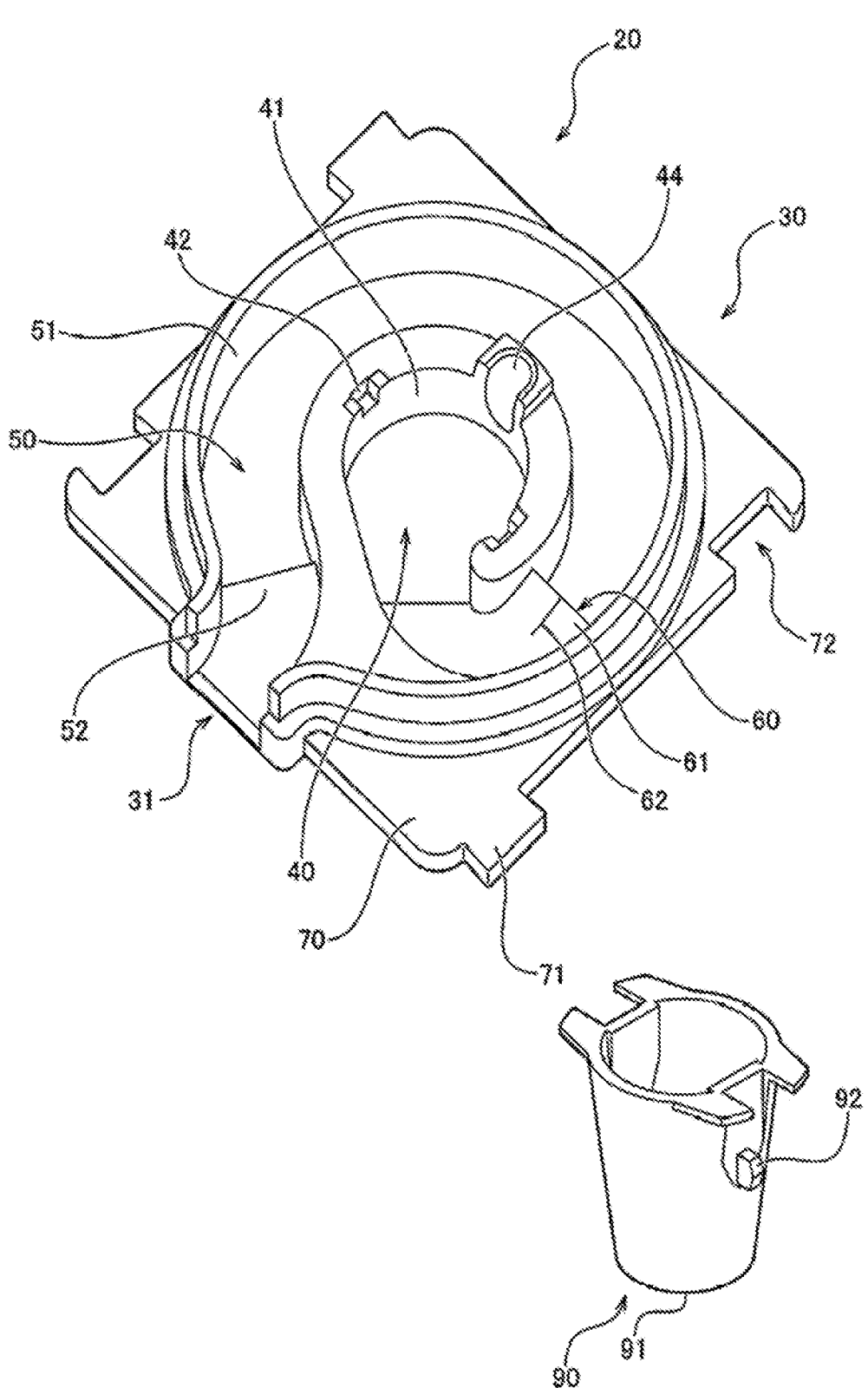
FIG. 1 is a perspective view of a main body of a device for evaluation of a chemical substance according to a first embodiment of the present invention.

A. Device for Evaluation of Chemical Substance:

FIG. 1 is a perspective view of a main body 30 of a device 20 for evaluation of a chemical substance according to a first embodiment of the present invention. In the present embodiment, the device 20 is for use in an evaluation test of the first pass effect in which small intestine cells and liver cells are used. However, the device 20 can be used also in evaluations of influences of various chemical substances on a living body (e.g., evaluations of in vivo pharmacokinetics, effects and a toxicity) as described later. The main body 30 includes a first compartment 40, a second compartment 50, a partition wall 60, and a base 70. The first compartment 40 is formed on an inner side of a wall portion 41 curved in a substantially round shape. A part of the wall portion 41 is open while swirling in a spiral state. On an outer side of the wall portion 41, there is formed a wall portion 51 that surrounds the wall portion 41 via a space from the wall portion 41. The wall portion 41 and the wall portion 51 form the second compartment 50 therebetween. That is, the second compartment 50 is disposed to at least partially surround the first compartment 40. In the present embodiment, a bottom portion of each of the first compartment 40 and the second compartment 50 is formed of a transparent member.

The partition wall 60 is formed to extend between the wall portion 41 of the first compartment 40 and the wall portion 51 of the second compartment 50. The first compartment 40 is separated from the second compartment 50 in the single device 20 by the partition wall 60. The partition wall 60 is formed with a wall height lower than a wall height of the wall portion 41 and the wall portion 51. Furthermore, the partition wall 60 is formed with a wall height higher than a wall height of an after-mentioned wall portion 52. The first compartment 40 communicates with the second compartment 50 via the partition wall 60 (i.e., communicates only by overflow of the partition wall 60), thereby forming a spiral flow path through which a perfusion fluid flows.

An insert 90 is inserted in the first compartment 40. The insert 90 is a cell culture container in which the cells are to be cultured, and is a commercially available transwell in the present embodiment. A bottom portion 91 of the insert 90 is formed of a porous membrane filter. Small intestine cells 96 are disposed on this porous membrane filter. The insert 90 is formed in a bottomed cylindrical shape. A pair of opposite projecting portions 92 are formed on an outer surface of the insert 90 (only one of the projecting portions 92 is shown in FIG. 1).

A pair of opposite slits 42 are formed at an upper end of the wall portion 41 forming the first compartment 40. Each slit 42 is formed in such a size that the projecting portion 92 is inserted in the slit. The slits 42 function as a support structure to support the insert 90 in a state where the insert 90 is inserted in the first compartment 40. In a state where the insert 90 is supported by the slits 42, a slight clearance through which the perfusion fluid flows is formed between the bottom portion 91 of the insert 90 and a bottom surface of the first compartment 40. This clearance is also utilizable to culture the cells.

Furthermore, a cutout portion 44 is formed at the upper end of the wall portion 41 forming the first compartment 40. The cutout portion 44 is formed in a substantially semicircular shape, and a cross-sectional area of the cutout portion decreases toward the bottom portion of the first compartment 40. The cutout portion 44 is positioned outside the insert 90 supported in the slits 42.

The partition wall 60 is formed with the wall height lower than the wall height of the wall portion 41 and the wall portion 51. In the present embodiment, the partition wall 60 has an inclined surface 61 inclined so that the wall height increases toward the second compartment 50, in the first compartment 40. According to such a configuration, a portion in which a liquid surface level rises due to surface tension in the vicinity of an upper end of the inclined surface 61 is longer than a vertical wall in a horizontal direction. Therefore, an amount of the perfusion fluid is adjusted so that the perfusion fluid flows from the first compartment 40 over the partition wall 60 into the second compartment 50 little by little, so that the flow of the perfusion fluid flowing from the first compartment 40 over the partition wall 60 into the second compartment 50 can be slowed down. As a result, it is possible to suppress concentration change of the chemical substance in the second compartment 50 which is caused by rapid fluctuation of the flow of the perfusion fluid.

Furthermore, according to the present embodiment, in the inclined surface 61, a groove 62 extending from a top of the inclined surface 61 toward a first compartment 40 side is formed. According to such a configuration, capillary phenomenon can move the perfusion fluid from the first compartment 40 to the second compartment 50 through the groove 62 little by little. Therefore, pulsation flow is inhibited from being generated when the perfusion fluid flows over the partition wall 60. As a result, it is further possible to suppress the concentration change of the chemical substance in the second compartment 50. In the present embodiment, the groove 62 is formed substantially in a center of the inclined surface 61, but the groove 62 may be formed along inclination of the inclined surface 61 from an arbitrary location to the top of the inclined surface 61. For example, the groove 62 may be formed in a connecting portion of the partition wall 60 with the wall portion 41 or the wall portion 51.

At a downstream end of the second compartment 50, the wall portion 52 extending between the wall portion 41 and the wall portion 51 is formed. The wall portion 52 is formed with the wall height lower than the wall height of the wall portion 41 and the wall portion 51. On a downstream side of the wall portion 52, an outlet 31 of the perfusion fluid is formed. Liver cells 97 are disposed in a bottom portion of the second compartment 50. The wall portion 52 described above is provided to store a medium solution in the second compartment 50, when the cells are cultured in the second compartment 50. When the wall portion 52 is not formed, for example, the outlet 31 may be closed with a seal, to store the medium solution in the second compartment 50. As clear from this description, in the present application, a term "compartment" means each of a plurality of regions in which the cells are arranged, the plurality of regions being separated from one another. For example, a part of each compartment may be opened as in the outlet 31 when the wall portion 52 is not formed.

The base 70 extends from a base portion of the wall portion 51 in the horizontal direction outside the wall portion 51. The base 70 includes two convex portions 71 and two concave portions 72. The convex portion 71 and the concave portion 72 have a complementary shape. The convex portion 71 and the concave portion 72 engage the adjoining bases 70 with each other, when a plurality of devices 20 are arranged side by side. That is, the convex portion 71 of one base 70 engages with the concave portion 72 of the other adjacent base 70. According to this configuration, the plurality of devices 20 can be easily fixedly arranged side by side.

Figure 2:
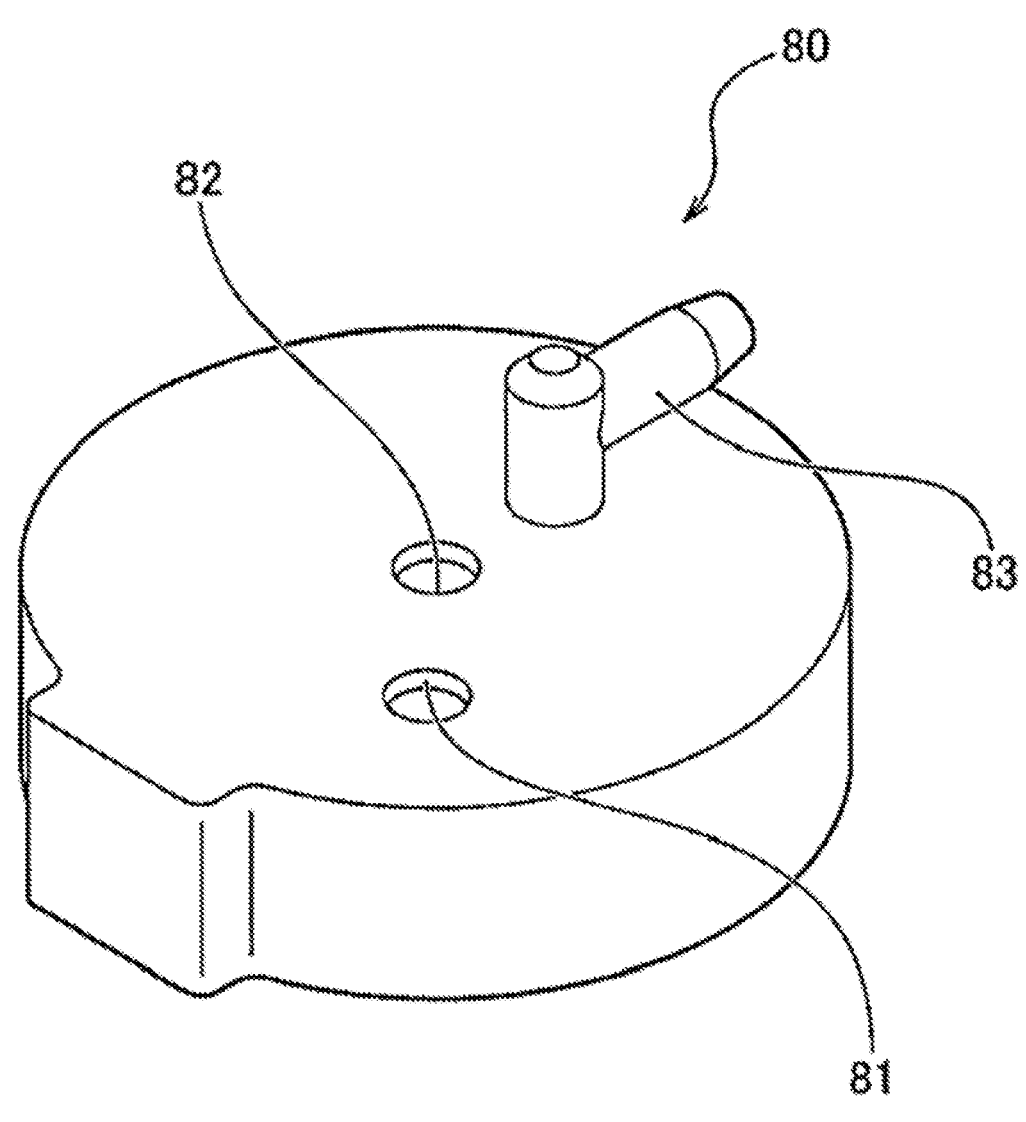
FIG. 2 is a perspective view of a cover of the device according to the first embodiment of the present invention.

The device 20 further includes a cover 80 to cover the first compartment 40 and the second compartment 50. In the present embodiment, the cover 80 is formed of a transparent member. FIG. 2 is a perspective view of the cover 80. As shown in the drawing, in an upper surface of the cover 80, a sampling hole 81 extending through the upper surface is formed. In the present embodiment, the sampling hole 81 is formed right above the first compartment 40 and is open in the first compartment 40. In place of or in addition to the sampling hole 81, a sampling hole that is open in the second compartment 50 may be formed.

Furthermore, in the upper surface of the cover 80, a chemical substance throw port 82 extending through the upper surface is formed. The chemical substance throw port 82 is provided to throw the chemical substance of the evaluation object into the first compartment 40. In the present embodiment, the chemical substance throw port 82 is formed substantially in a center of the cover 80, and right under the port, the first compartment 40 or the insert 90 is located. Consequently, the chemical substance thrown through the chemical substance throw port 82 is thrown into the first compartment 40 when the insert 90 is not installed, and thrown into the insert 90 when the insert 90 is installed. Furthermore, an inlet port 83 is formed in the cover 80. The inlet port 83 is provided to inject the perfusion fluid into the first compartment 40. The inlet port 83 is connected to, for example, a syringe pump to supply the perfusion fluid. An inner passage of the inlet port 83 is open right above the cutout portion 44. Since the cutout portion 44 is located outside the insert 90, the inlet port 83 communicates with a portion of the first compartment 40 outside the insert 90.

Figure 3:
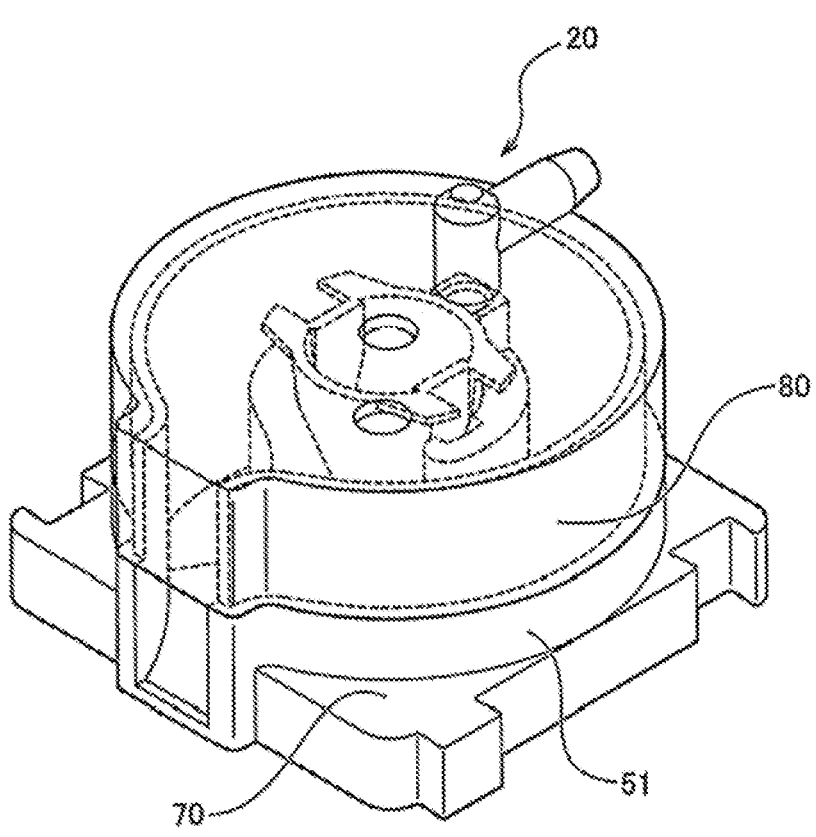
FIG. 3 is a perspective view of the device having the main body to which the cover is mounted.

That is, the perfusion fluid to be supplied from the inlet port 83 is supplied into the first compartment 40 or the portion of the first compartment outside the insert 90 via the cutout portion 44. The cover 80 is mounted on the wall portion 51 as shown in FIG. 3.

According to the cover 80, a test environment (i.e., the first compartment 40 and the second compartment 50) can be easily kept in a clean state during the evaluation test. Additionally, the perfusion fluid can be easily sampled through the sampling hole 81. Furthermore, the chemical substance can be easily thrown through the chemical substance throw port 82, and the perfusion fluid can be easily injected through the inlet port 83.

Figure 4A:
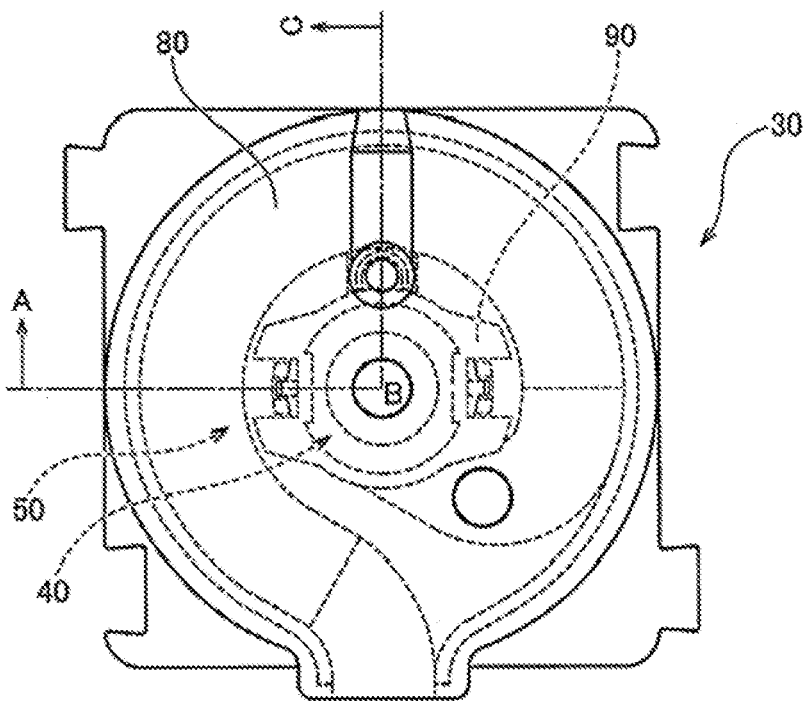
FIG. 4A is a top plan view of the device.
Figure 4B:
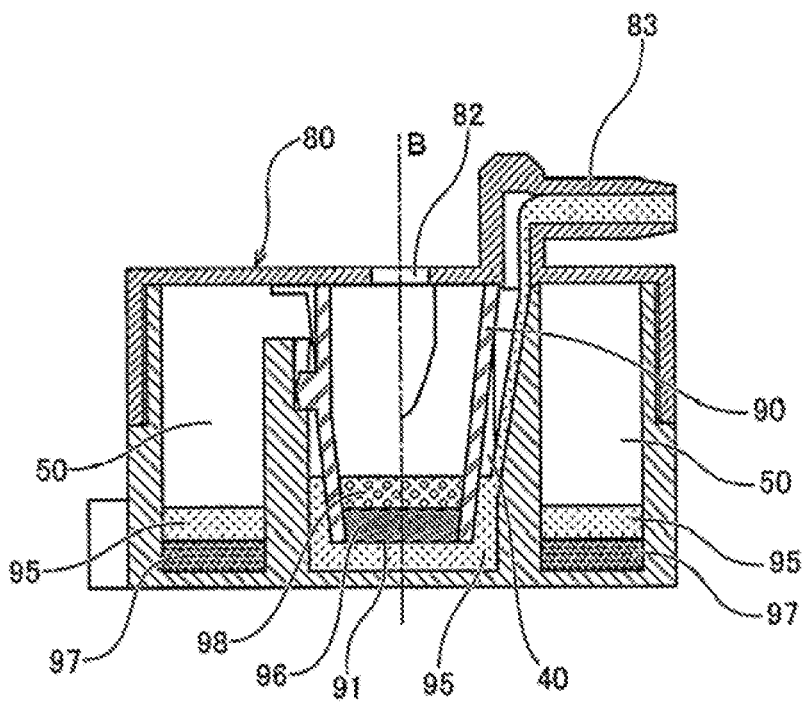
FIG. 4B is a cross-sectional view of the device.

FIG. 4A is a top plan view of the device 20. FIG. 4B is a cross-sectional view of the device 20 based on arrow angles A to C of FIG. 4A, and shows a behavior during the evaluation test of the first pass effect. A perfusion fluid 95 continuously injected through the inlet port 83 flows into the first compartment 40, flows around the insert 90 and in a region under the bottom portion 91 of the insert 90, and flows over the partition wall 60 into the second compartment 50. In the second compartment 50, the perfusion fluid flows along a region on the liver cell 97 disposed in the bottom portion of the second compartment 50, flows over the wall portion 52, and is discharged from the outlet 31. Furthermore, the chemical substance thrown inside through the chemical substance throw port 82 mixes with a medium solution 98 in the insert 90, permeates the small intestine cells 96 and the bottom portion 91 (the porous membrane filter), and shifts to the perfusion fluid 95 in the first compartment 40. Then, the chemical substance flows through the region on the liver cells 97 in accordance with the above described flow of the perfusion fluid 95, and is metabolized by the liver cells 97.

Figure 5:
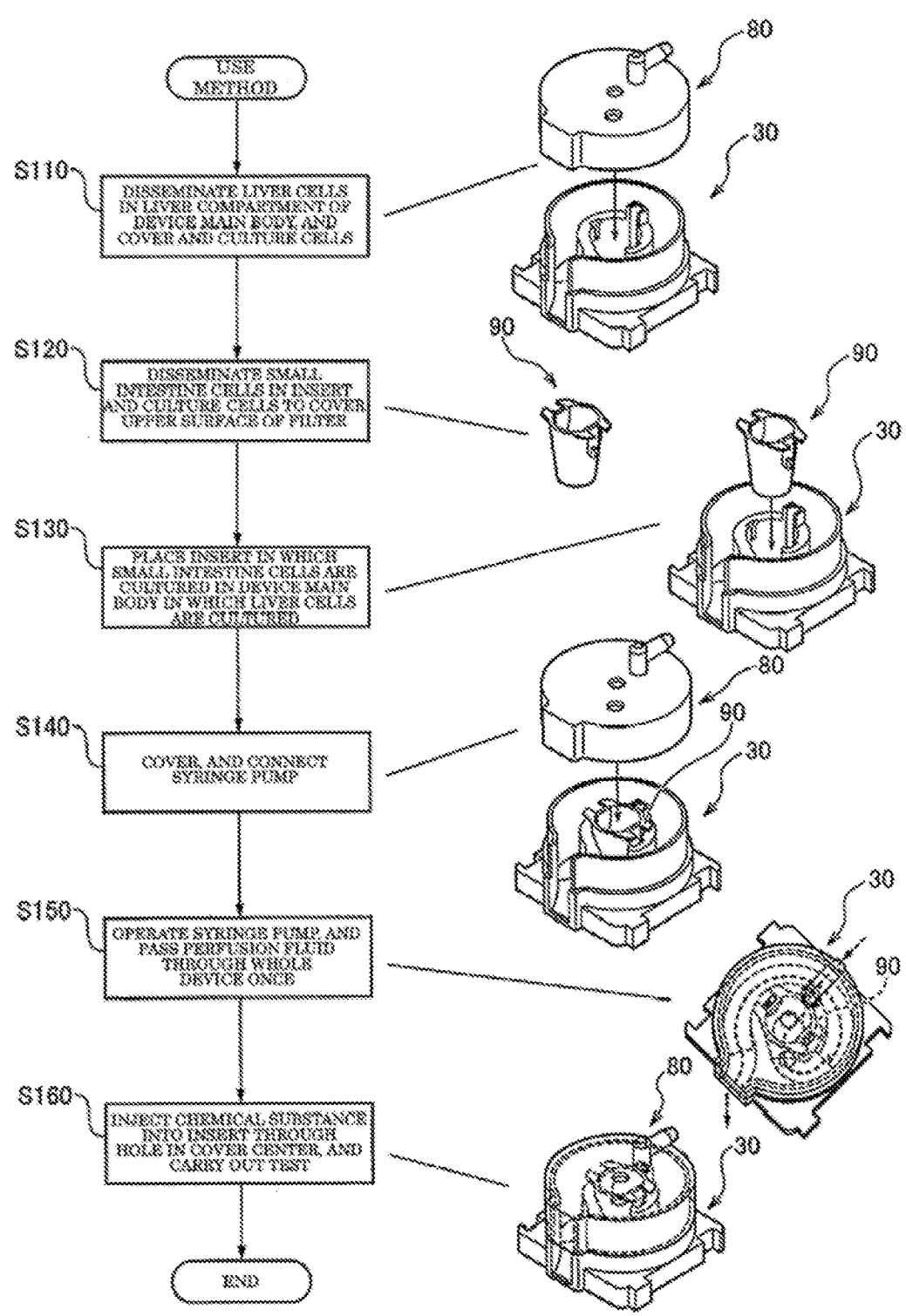
FIG. 5 is an explanatory view showing a procedure in performing an evaluation test by use of the device.

FIG. 5 is an explanatory view showing a procedure in performing the evaluation test of the first pass effect by use of the device 20. In this test, first, the liver cells 97 are disseminated in the second compartment 50 of the main body 30, covered with the cover 80 and cultured (step S110). Next, the small intestine cells 96 are disseminated in the insert 90 and cultured to cover an upper surface of the bottom portion 91 (the porous membrane filter) (step S120). Next, the insert 90 in which the small intestine cells 96 are cultured is inserted in the main body 30 (more particularly, the first compartment 40) in which the liver cells 97 are cultured (step S130). Next, the main body 30 is covered with the cover 80, and the inlet port 83 is connected to the syringe pump (step S140). Next, the syringe pump is operated, and the perfusion fluid 95 is passed through the whole device 20 once (i.e., the whole first compartment 40 and second compartment 50) (step S150). Then, the chemical substance is thrown into the insert 90 through the chemical substance throw port 82 formed in the center of the cover 80, and the test is carried out in a state where the main body is covered with the cover 80 (step S160).

In this test, the perfusion fluid 95 can be sampled through the sampling hole 81, and a degree of mixture of chemical substance components in the solution can be confirmed. Alternatively, the perfusion fluid 95 discharged from the outlet 31 can be sampled over time and inspected. Furthermore, the small intestine cells 96 and the liver cells 97 can be observed via the bottom portions (the transparent members) of the first compartment 40 and the second compartment 50 with a microscope. Additionally, the small intestine cells 96 and the liver cells 97 can be observed via the cover 80 (the transparent member) with the microscope.

Figure 6:
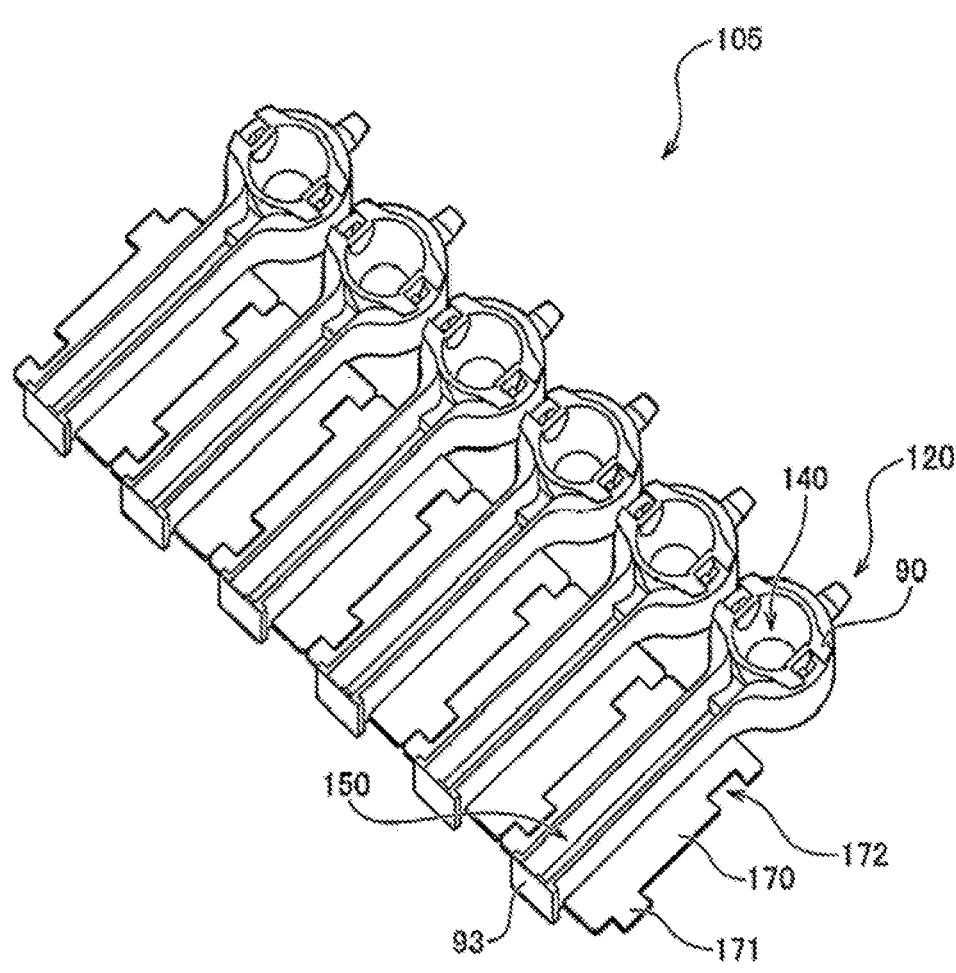
FIG. 6 is a perspective view of a kit for evaluation of a plurality of chemical substances according to a second embodiment of the present invention.

FIG. 6 is a perspective view of a kit 105 for evaluation of a chemical substance according to a second embodiment. Hereinafter, description will be made only as to different respects of the kit 105 from the first embodiment. The kit 105 includes a plurality of devices 120 for evaluation of chemical substances.

Figure 7:
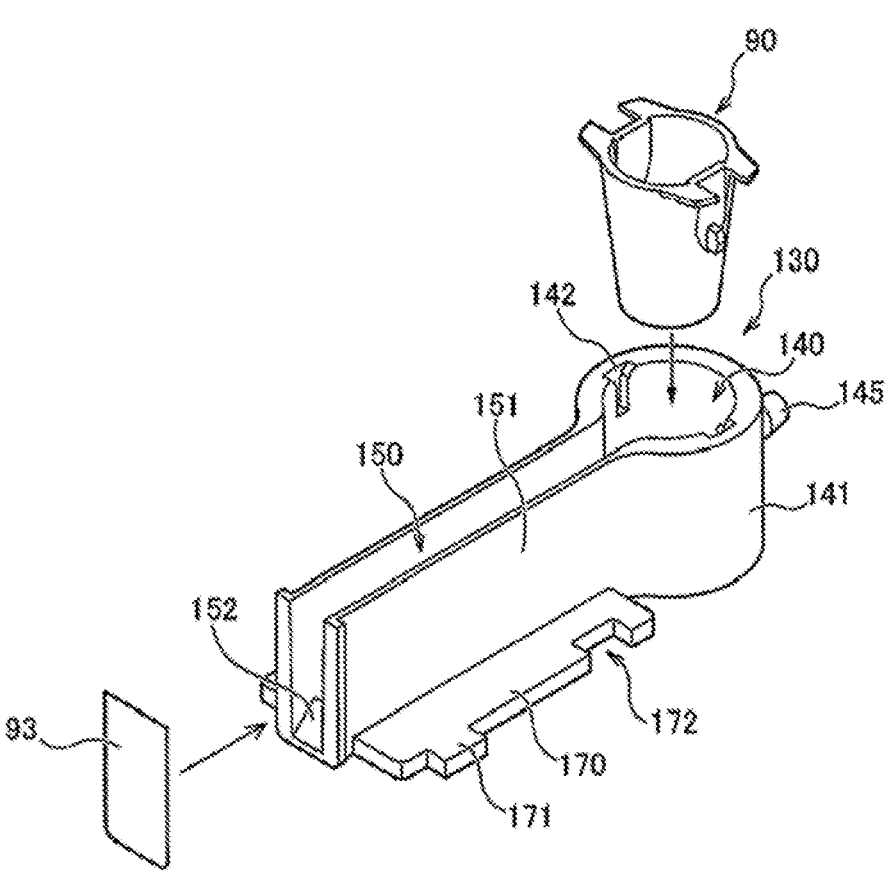
FIG. 7 is a perspective view of a main body of FIG. 6.
Figure 8:
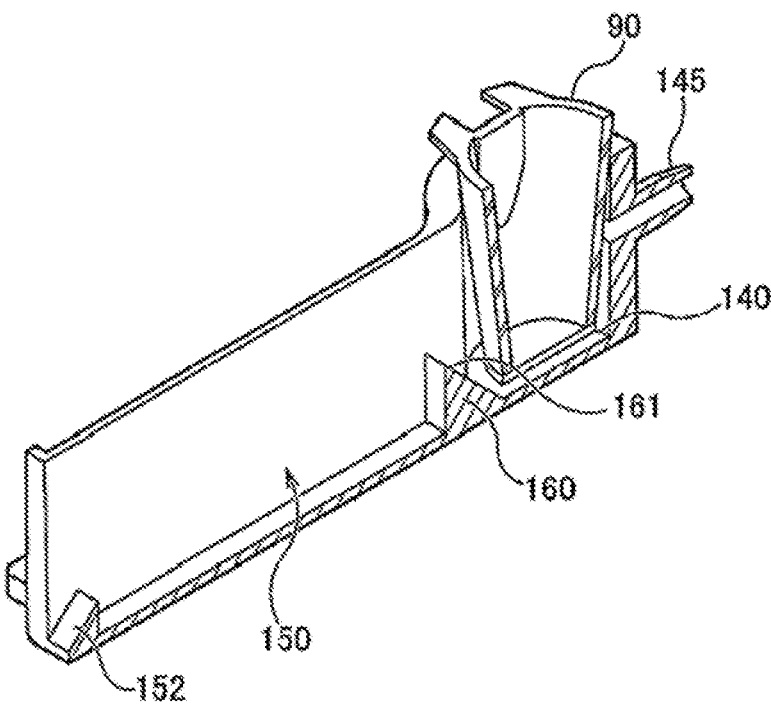
FIG. 8 is a cross-sectional perspective view showing an interior of the main body of FIG. 7.

FIG. 7 is a perspective view of a main body 130 of the device 120 and an insert 90. FIG. 8 is a cross-sectional perspective view of the main body 130 and the insert 90. The device 120 is different from the device 20 of the first embodiment in its shape. Specifically, as shown in FIG. 7, the device 120 includes a first compartment 140 formed by a substantially cylindrical wall portion 141, and a second compartment 150 formed by two rectangular wall portions 151 continuous with the wall portion 141. That is, in the present embodiment, the first compartment 140 and the second compartment 150 are arranged side by side. The second compartment 150 has an elongate shape extending from the columnar first compartment 140. As shown in FIG. 8, the first compartment 140 and the second compartment 150 are separated by a partition wall 160 having an inclined surface 161 in the same manner as in the first embodiment. Furthermore, a wall portion 152 is formed at a downstream end of the second compartment 150. When the wall portion 152 is not formed, as shown in FIG. 7, a seal 93 to seal the second compartment 150 during cell culture in the second compartment 150 may be attached on a downstream side from the wall portion 152.

In the present embodiment, the device 120 does not include any covers. Consequently, as shown in FIG. 7, an inlet port 145 to be connected to a syringe pump so that a perfusion fluid is injected through the port is formed in the wall portion 141. However, the device 120 may include a cover similar to the cover of the first embodiment. In this case, the cover does not have to include the inlet port. The inlet port 145 directly communicates with an interior of the first compartment 140 as shown in FIG. 8. A lower end of the inlet port 145 may be located at a position higher than the partition wall 160. In this case, a level of the perfusion fluid in the first compartment 140 may be located below the inlet port 145. Consequently, even when a flow velocity of the perfusion fluid to be supplied from the syringe pump through the inlet port 145 into the first compartment 140 is slow, it is possible to prevent shift of the chemical substance from the first compartment 140 to the inlet port 145 due to a concentration gradient of the chemical substance between the perfusion fluid in the first compartment 140 and the perfusion fluid in the inlet port 145. Furthermore, a pair of slits 142 to support the insert 90 are formed in the wall portion 141 in the same manner as in the first embodiment.

A base 170 extends from a base portion of the wall portion 151. The base 170 has a width approximately equal to an outer diameter of the wall portion 141. The base 170 includes convex portions 171 and concave portions 172 in the same manner as in corresponding first embodiment, and as shown in FIG. 6, the plurality of devices 120 can be coupled in a direction perpendicular to a direction in which the first compartment 140 and the second compartment 150 are arranged side by side. According to the kit 105, the plurality of devices 120 can be compactly arranged side by side.

Figure 9:
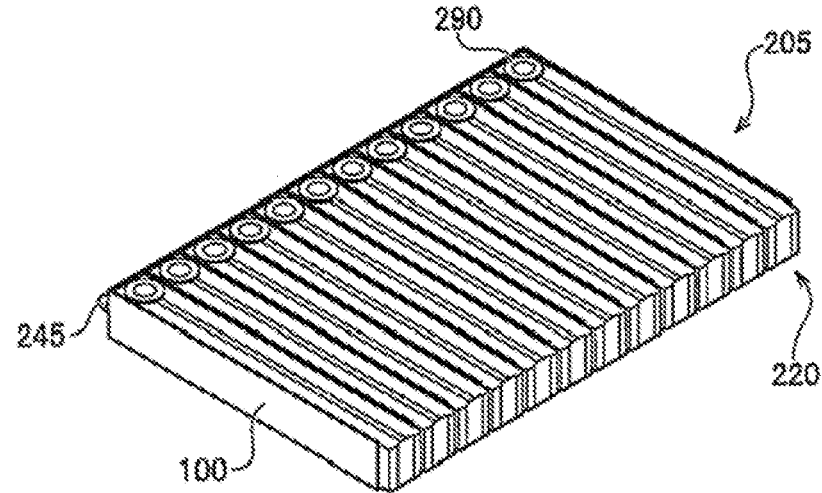
FIG. 9 is a perspective view of a kit for evaluation of a chemical substance according to a third embodiment of the present invention.
Figure 10:
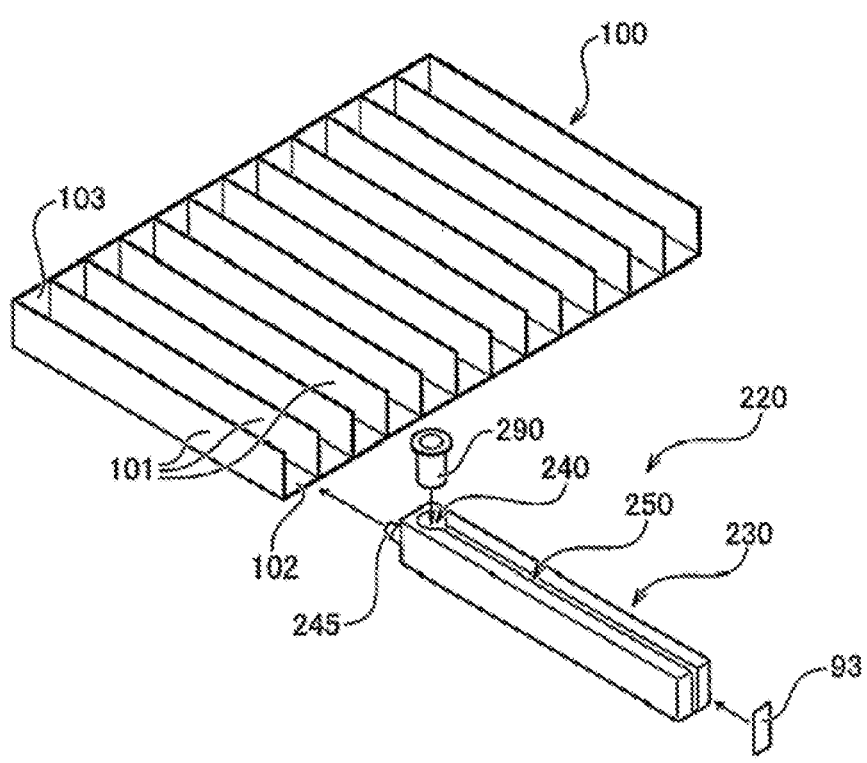
FIG. 10 is an exploded perspective view of the kit of FIG. 9.

FIG. 9 is a perspective view of a kit 205 for evaluation of a chemical substance according to a third embodiment. FIG. 10 is an exploded perspective view of the kit 205. Hereinafter, description will be made only as to different respects of the kit 205 from the second embodiment. The kit 205 includes a plurality of devices 220 for evaluation of the chemical substances. As shown in FIG. 10, a main body 230 of the device 220 has a substantially rectangular parallelepiped outer shape, and in the main body, a substantially cylindrical first compartment 240 and an elongate second compartment 250 are arranged side by side in the same manner as in the second embodiment. An insert 290 is inserted in the first compartment 240. An upper edge portion of the insert 290 is formed in a flange shape, and the insert is different from the insert 90 of the first embodiment only in that the flange-like portion is mounted on an upper surface of the main body 230. An inlet port 245 that directly communicates with the first compartment 240 is formed in the main body 230 in the same manner as in the second embodiment. The device 220 does not include any covers. However, the device 220 may include a cover similar to the cover of the first embodiment. In this case, the cover does not have to include the inlet port.

The kit 205 further includes a case 100 that stores the plurality of devices 220 in a state where the respective devices are arranged in a lateral direction. The case 100 includes a bottom portion 102 and a plurality of partitions 101. The plurality of partitions 101 are disposed apart from each other so that the device 220 can be slidably inserted between two adjoining partitions 101. A through hole (not shown in the drawing) into which the inlet port 245 is inserted is formed in a wall portion 103. According to the kit 205, the plurality of devices 220 can be compactly arranged side by side, and can be also easily fixedly arranged side by side. The bottom portion 102 of the case 100 may be formed of a transparent member so that the cells can be observed. Furthermore, as an alternative configuration, the case 100 does not have to include the bottom portion 102. That is, a region corresponding to a bottom portion position of each compartment of the device 220 may be of an open type. Also according to this configuration, the cells in each compartment can be observed.

Figure 11:
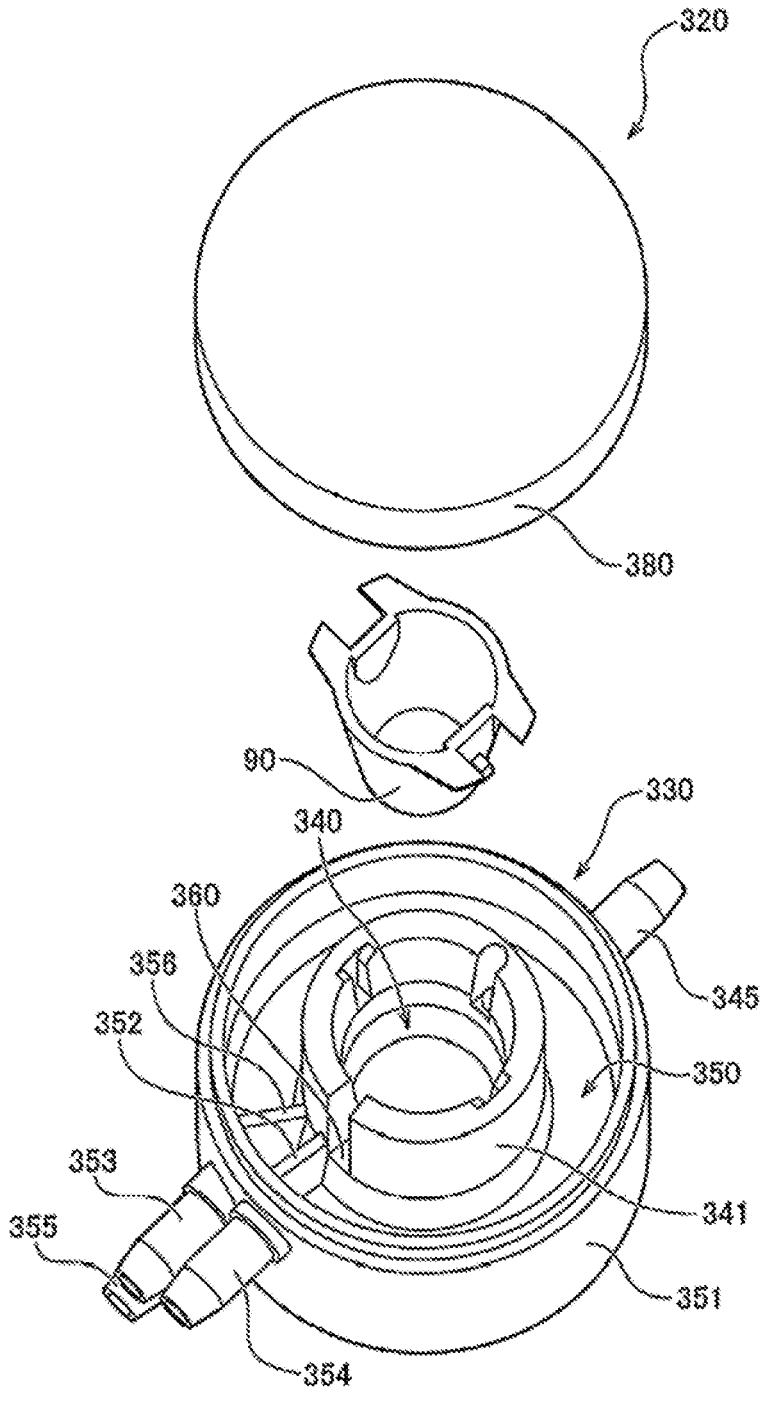
FIG. 11 is an exploded perspective view of a device for evaluation of a chemical substance according to a fourth embodiment of the present invention.
Figure 12:
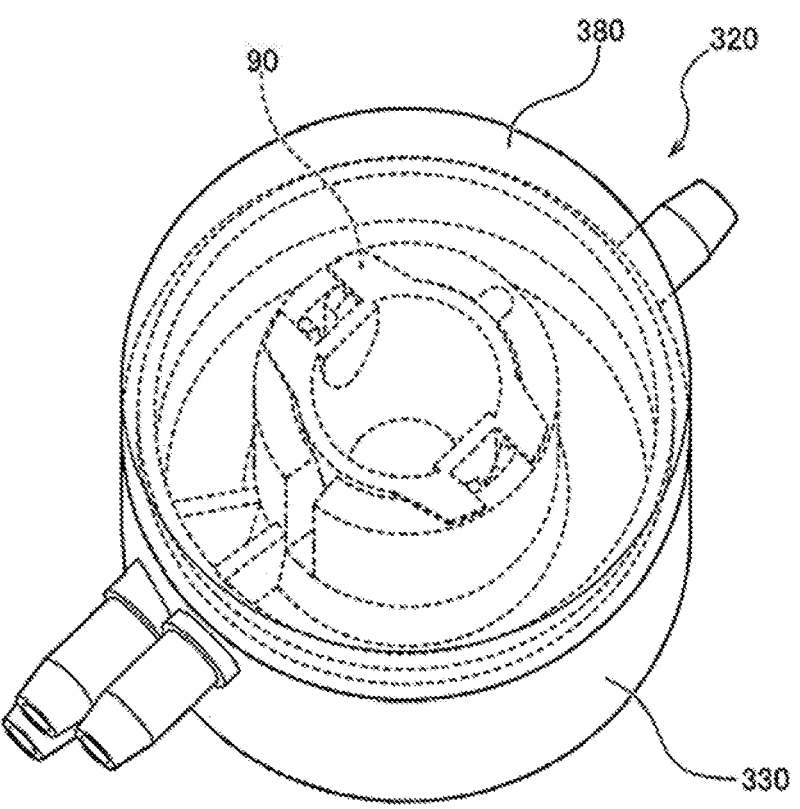
FIG. 12 is a perspective view of the device of FIG. 11.
Figure 13:
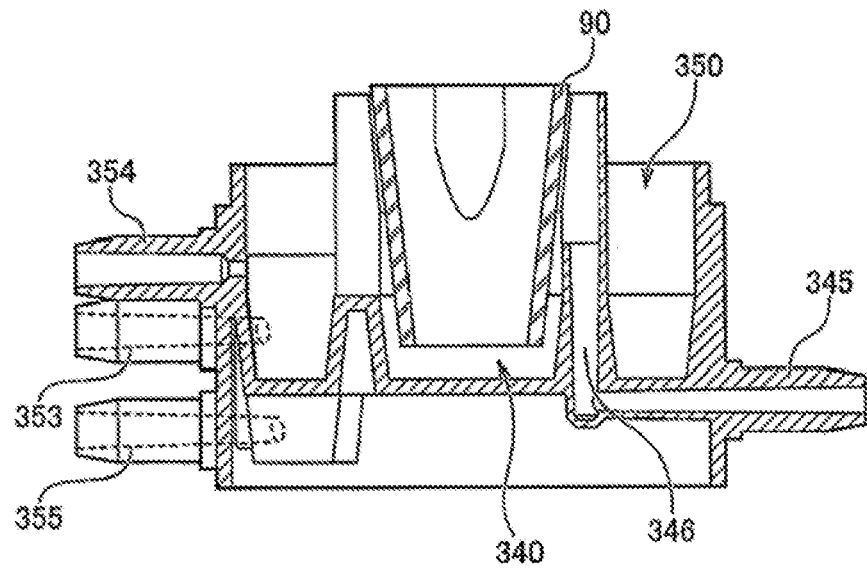
FIG. 13 is a cross-sectional view of a main body of the device of FIG. 11.

FIG. 11 is an exploded perspective view of a device 320 for evaluation of a chemical substance according to a fourth embodiment. FIG. 12 is a perspective view of the device 320. FIG. 13 is a cross-sectional view of a main body 330 of the device 320. Hereinafter, description will be made only as to different respects of the device 320 from the first embodiment. As shown in FIG. 11, the main body 330 of the device 320 includes a substantially cylindrical wall portion 341, and a substantially cylindrical wall portion 351 disposed to surround the wall portion 341 outside the wall portion 341. A first compartment 340 is formed inside the wall portion 341, and a second compartment 350 is formed between the wall portion 341 and the wall portion 351 and concentrically with the first compartment 340. The first compartment 340 and the second compartment 350 are separated by a partition wall 360.

In the second compartment 350, there is formed a dividing wall 352 that divides a vicinity of the partition wall 360 into an upstream end and a downstream end of the second compartment 350. As shown in FIG. 13, an inlet port 345 to inject a perfusion fluid is formed in the wall portion 351. The inlet port 345 extends below the second compartment 350 to communicate with an interior of the first compartment 340 via a communication hole 346. As shown in FIG. 11, in the wall portion 351, a discharge port 353 to discharge the perfusion fluid is formed at a position corresponding to the downstream end of the second compartment 350. When the perfusion fluid is continuously supplied from the inlet port 345, the perfusion fluid flows through the first compartment 340 and the second compartment 350 and is discharged from the discharge port 353.

Further in the wall portion 351, a circulation inlet port 354 and a circulation outlet port 355 to be connected to pumps (e.g., tube pumps) are formed to circulate the perfusion fluid through a route extending in the second compartment 350. The circulation inlet port 354 is formed at a position corresponding to the upstream end of the second compartment 350, and the circulation outlet port 355 is formed at a position corresponding to the downstream end of the second compartment 350. A wall portion 356 is formed on an upstream side of the discharge port 353 and the circulation outlet port 355. The wall portion 356 is provided to store a medium solution in culturing cells in the second compartment 350, and corresponds to the wall portion 152 shown in FIG. 7.

A certain amount of the perfusion fluid is stored in the first compartment 340 and the second compartment 350, and then, the perfusion fluid can circulate via the circulation inlet port 354 and the circulation outlet port 355. Specifically, first, the supply of the perfusion fluid from the inlet port 345 is stopped, and the discharge port 353 is closed. Afterward, the perfusion fluid discharged from the circulation outlet port 355 flows through the circulation inlet port 354 into the second compartment 350 again via the pump. Consequently, the perfusion fluid circulates through the second compartment 350. According to this configuration, it is possible to evaluate a long term influence of the chemical substance on the cells disposed in the second compartment 350 under an environment that imitates a circulatory system of an animal.

As shown in FIG. 11, in the present embodiment, a cover 380 does not have any sampling holes or any chemical substance throw ports. Consequently, the cover 380 is removed during sampling and during chemical substance throwing.

In the above described embodiments, the insert is not essential, and the cells may be disposed directly in the first compartment. Furthermore, at least one of the first compartment and the second compartment of the device may include two or more sub-compartments separated in parallel. In this case, a partition wall that separates the compartments from each other may be provided in each sub-compartment. Furthermore, the device may include three or more compartments that communicate in series. In this case, two adjoining compartments among the three or more compartments are separated by a partition wall. At least one of the three or more compartments may include two or more sub-compartments separated in parallel.

B. Use Mode of Device

In the above described device, cells disseminated to a plurality of compartments can be combined to imitate human organs and tissues. Therefore, it is possible to model, for example, an oral first pass effect (intestinal epithelial cell/liver cell), a blood-brain barrier (brain capillary endothelial cell/nerve cell), a blood-placental barrier (syncytiotrophoblast (a trophoblast syncytial cell) layer/fetal tissue or undifferentiated tissue), an intestinal tract (intestinal epithelial cell)/liver (liver cell)/blood-brain barrier (brain capillary endothelial cell/nerve cell), an intestinal tract (intestinal epithelial cell)/liver (liver cell)/kidney (renal tubular epithelial cell), or the like.

In one aspect of the present invention, a removal cell culture container (insert) having a porous membrane filter in a bottom surface of the container may be mounted to a device. When the cells are cultured in the cell culture container, a cell membrane (a cell sheet) is preferably formed on (or under) the porous membrane filter. A liquid such as a cell culture fluid or a perfusion fluid and small molecules (the chemical substance, etc.) dissolved or suspended in the liquid permeate the porous membrane filter, but the cells do not permeate the porous membrane filter. When the chemical substance and a liquid carrier are separated by the cell sheet, the chemical substance permeates the cell sheet, and dynamics of the chemical substance that shifts to the liquid carrier can be directly evaluated. The chemical substance permeation from the cell sheet can directly reflect influences and the like of chemical substance metabolism, chemical substance interaction and gene polymorphism, in addition to chemical substance absorption and excretion in the small intestine, blood-brain barrier, placenta, lung, kidney and others.

(1) Chemical Substance

There are not any special restrictions on a type of chemical substance applicable to the device. The chemical substance applicable to the device is any chemical substance that may be applied to a living body. The chemical substance may be a liquid, or a solid or a semisolid that can be dissolved or suspended in the cell culture fluid, the perfusion fluid or the like. Examples of the chemical substance include pharmaceuticals, perfumery (cosmetics), food additives, pesticide, or candidate substances thereof. The chemical substance includes a compound, a nucleic acid, a peptide, a protein (an antibody or the like), a metal or the like. The chemical substance may be artificially synthesized or naturally derived and obtained from a microorganism, a plant, an animal or the like.

The chemical substance to be provided to the device may be an active component itself that can influence the living body. Alternatively, the chemical substance to be provided to the device may be a composition or an agent form including a carrier applicable to the living body, a vehicle or the like to be applied to the living body in addition to the active component. For example, there can be used the carrier or the vehicle commonly for use in preparation of a pharmaceutical composition for oral administration or parenteral administration (transdermal administration, subcutaneous administration, intraperitoneal administration or the like). Examples of an appropriate unit form include forms for the oral administration, such as a tablet, a soft or hard capsule, powder or granules in a sachet, a liquid, a suspension and an emulsion; and forms for the parenteral administration, such as an injection, a drip, a patch, an aerosol, an eye drop, an eye ointment, an ointment, a liniment, a lemonade, a flow extract, a lotion, a percutaneous absorption type formation, and a paste.

Alternatively, the chemical substance to be applied to a cell culture container (insert) device does not have to be the chemical substance itself of the active component that can influence the living body, and may be a substance or a living thing that produces or releases the chemical substance. Examples of "the material or the living thing that produces or releases the chemical substance" non-restrictively include enteric flora, and nucleic acids (nucleic acid medicines, etc.). Even when "the material or the living thing that produces or releases the chemical substance" is not carried by the perfusion fluid, the active component (chemical substance) produced/released by the material or the living thing is dissolved or suspended in the cell culture fluid or the perfusion fluid and is then carried. Such "substance or living thing that produces or releases the active component" may be inclusively referred to as "the chemical substance" herein.

A plurality of types of chemical substances may be applied to the above device. For example, the plurality of types of chemical substances may be applied to the cell culture container simultaneously or over time, and then the container may be inserted in the first compartment. In the present description and claims, description that "the chemical substance is applied to the first compartment" includes both of the insertion of the cell culture container in the first compartment and the application of the chemical substance to the cell culture container, and the application of the chemical substance directly to the first compartment without using the cell culture container, unless otherwise specified. Consequently, it is possible to check an influence of a combination of the plurality of types of chemical substances on the living body when the combination is administered to the same organ or tissue simultaneously or over time. Alternatively, the cell culture container may be inserted in the first compartment, the chemical substance may be applied to the cell culture container, and another or the same chemical substance may be applied to the second or later compartment. Consequently, it is possible to check the influence of the chemical substance on the living body when the combination of the plurality of types of chemical substances or one type of chemical substance is administered to different organs or tissues simultaneously or over time.

(2) Cell

There are not any special restrictions on a type of cell that is applicable to the above device. The cell to be applied to the device may be an adherent cell that adheres to a bottom surface or a wall surface of a filter or a container, or a floating cell that floats in the cell culture fluid or the perfusion fluid. According to the above device, when the compartments containing the cells are continuously connected, a state closer to an environment of an organ or a tissue of a living body can be reproduced. It is preferable to use a cell suitable for reproduction of a configuration of the organ or the tissue to be evaluated. It is also possible to use a cell line established as a model cell of each organ or tissue. For example, without any limitations, Caco-2 cell may be used as a model cell of an intestinal epithelial cell, HepG2 cell may be used as a model cell of a liver cell, NSC-34 cell line (manufactured by CELLutions BIOSYSTEMS Co., Ltd. and distributed by COSMO BIO Co., Ltd.) may be used as a model cell of a nerve cell, a human immortalized capillary endothelial cell may be used as a model cell of a brain capillary endothelial cell, and genetically engineered Mardin-Darby canine kidney (MDCK) cell line may be used as a model cell of a renal tubular epithelial cell. Alternatively, a cell induced to differentiate from a human induced pluripotent stem cell (iPS cell) or a three-dimensional organism (organoid or spheroid) prepared by induced differentiation from the iPS cell may be used. A model cell of a blood-placental barrier (syncytiotrophoblast (a trophoblast syncytial body)) can be prepared, for example, by using a human placenta as described, for example, in Reproductive Biology and Endocrinology (2015) 13:71. A genetically manipulated cell line may be also used.

The cells may be disseminated in the cell culture container. When the cells are adherent cells that cannot pass through the porous membrane filter and that are not carried by the perfusion fluid, the cells adhere to an upper surface of the porous membrane filter of the cell culture container, and can form a cell sheet. Alternatively, the cells may be disseminated in the first compartment. The adherent cells can adhere to a lower surface of the porous membrane filter of the cell culture container or to a bottom surface of the container of the first compartment, and can form the cell sheet. In the present description and claims, description "the cells are disseminated (disposed) in the first compartment" includes both of the dissemination of the cells in the cell culture container and the insertion of the cell culture container in the first compartment, and the dissemination of the cells in the first compartment, unless otherwise specified. Alternatively, the cells may be disseminated in the second or later compartment.

Different types of cells can be disseminated in the cell culture containers and compartments, respectively. Alternatively, two or more types of cells may be disseminated in one container or compartment.

(3) Cell Culture Container (Insert)

A known cell culture container (insert) can be used. Examples of the container include Culture Insert manufactured by Falcon Corporation, and Millicell Cell Culture Insert manufactured by Merck Millipore KGaA. The porous membrane filter is preferably made of a material such as polycarbonate (PC), polyester or polyethylene terephthalate (PET), or polytetrafluoroethylene (PTFE), and includes a plurality of open holes having a diameter of preferably from about 0.1 μm to about 10.0 μm and more preferably from about 0.2 μm to 8.0 μm.

The present invention also includes an organ model in which the cells of one or more organs are applied to the above device. The present invention also includes use of the above device or the above organ model in an evaluation method of the chemical substance.

(4) Organ (Intestinal Tract and Liver)-Model (Hepatitis Model by Human Hepatitis B Virus)

A configuration of the model in which the above device is used is an organ (an intestinal tract and a liver)-model (a hepatitis model by a human hepatitis B virus).

Intestinal epithelial cells are involved in an intestinal immune system in various ways. When an intestinal epithelial cell layer is injured due to inflammatory cytokines, peroxides or the like, immune cells around the layer are activated, to repair the epithelial layer and remove foreign matter. Excessive immune response causes inflammation in an intestinal tissue. On the other hand, production of the inflammatory cytokines of the intestinal epithelial cells is one of important factors for inflammatory response, and assumes an initial stage of the immune response. The inflammatory cytokines show the immune response themselves, and also have a function of inducing a response of another immunocompetent cell.

The orally administered chemical substance is absorbed by the intestinal epithelial cells, and carried to the liver via a blood vessel of a portal vein system. The blood vessel of the portal vein system is a blood vessel that collects blood of abdominal organs and enters the liver, and includes a superior mesenteric vein from the whole small intestine, cecum, ascending colon and transverse colon, an inferior mesenteric vein from a descending colon and sigmoid colon, and a splenic vein from a spleen.

Figure 14A:
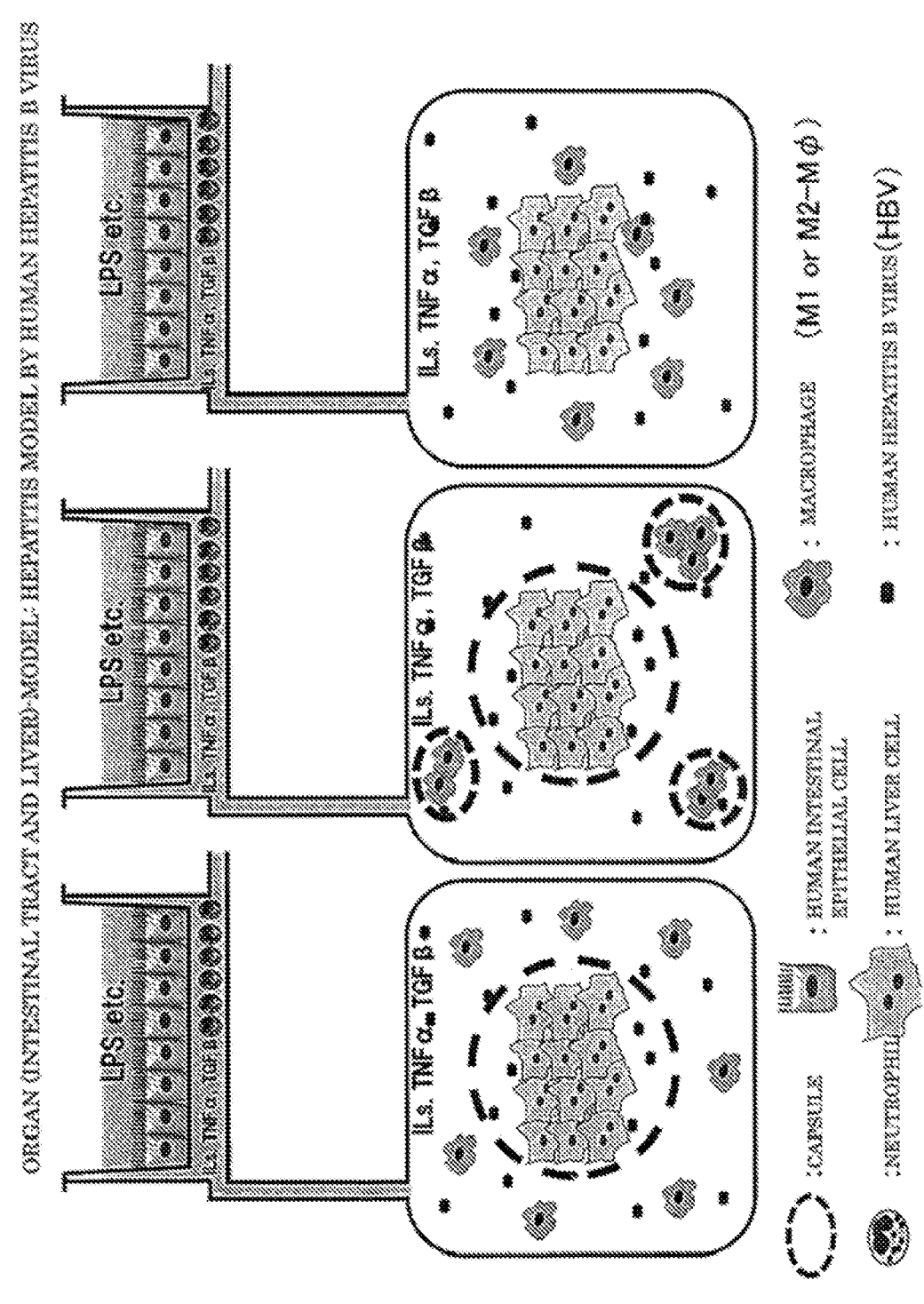
FIG. 14A is an example of an organ (an intestinal tract and liver)-model (a hepatitis model by a human hepatitis B virus).
Figure 14B:
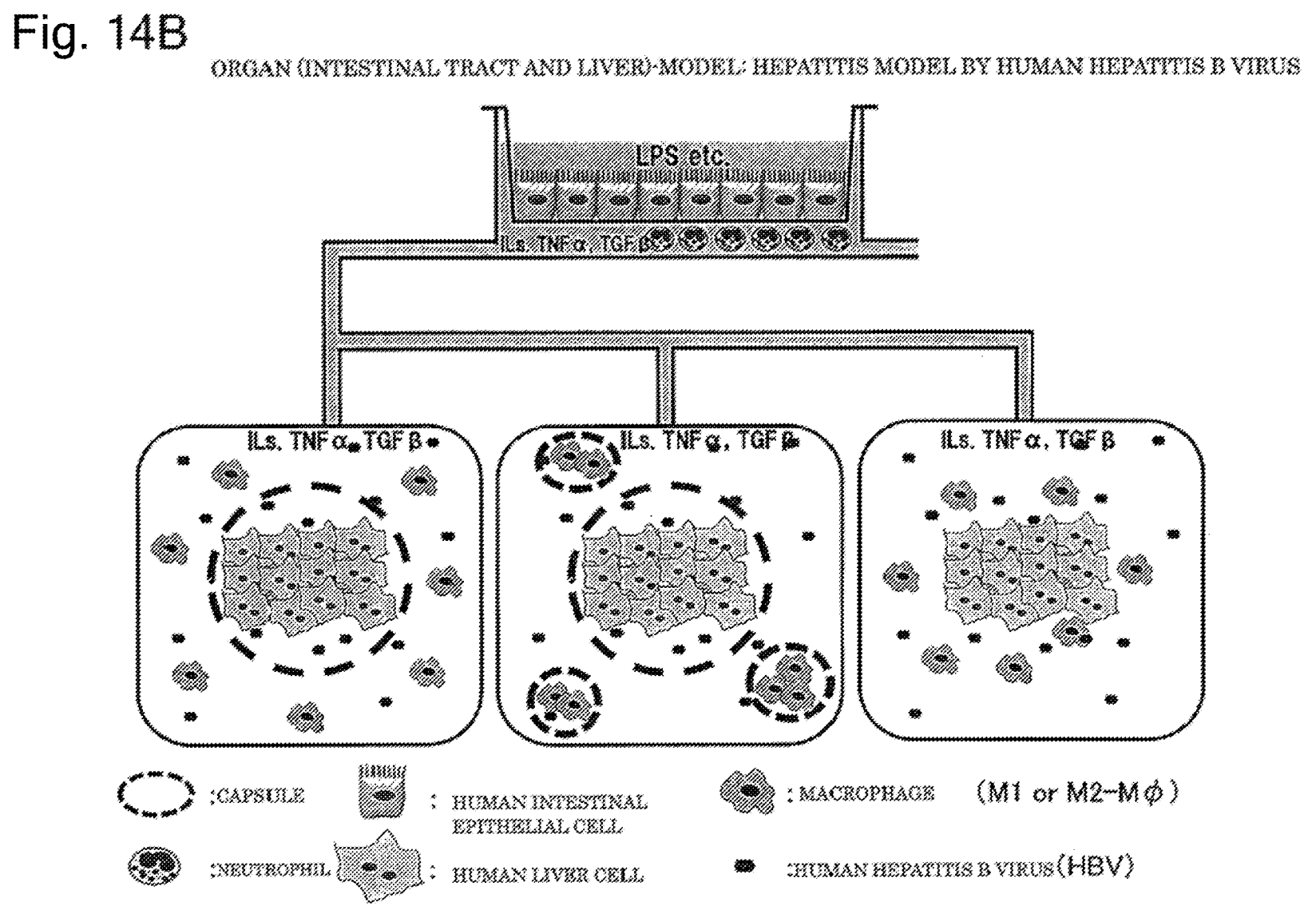

FIG. 14A and FIG. 14B shows an example of the organ (the intestinal tract and the liver)-model (the hepatitis model by the human hepatitis B virus). This example is a model in a state where the liver cells are infected with the human hepatitis B virus (HBV) to cause inflammation. Human intestinal epithelial cells form a cell sheet on the porous membrane filter of the cell culture container. A cell culture solution contains an enteric flora metabolite (an enteric flora-produced substance), lipopolysaccharide (LPS) and the like. Due to an inflammatory condition, inflammatory cytokines such as interleukins (iLs), tumor necrosis factor (TNF) a and transforming growth factor (TGF) β and a neutrophil as one type of white blood cell are present in the perfusion fluid. The perfusion fluid from the first compartment is supplied to the second compartment. In the second compartment, the human liver cells and macrophages (M1 or M2-MQ) are present. The macrophage is one type of white blood cell and a migratory phagocyte. The liver cells in the second compartment are infected with HBV, and form a model to evaluate conditions that easily cause the hepatitis most. Furthermore, for example, when the chemical substance (e.g., a pharmaceutical candidate substance) is added to the cell culture solution, a compound passes through the intestinal epithelial cells, and an influence of the compound on the HBV with which the liver cells are infected can be evaluated. The liver cells may be infected with a human hepatitis C virus (HCV) in place of the HBV.

FIG. 14A is a configuration in which there are a plurality of independent combinations of the first compartment and the second compartment. In the second compartment, a human liver cell capsule is formed in a first combination (left in FIG. 14A), a human liver cell capsule and a macrophage capsule are separately formed in a second combination (middle in FIG. 14A), and both the human liver cells and the macrophages are collectively encapsulated or co-cultured in a third combination (right in FIG. 14A). A capsule is a membrane through which the cells cannot pass and, for example, the HBV, HCV or protein can pass.

FIG. 14B is a configuration in which the second compartment has a plurality of sub-compartments. The perfusion fluid from the first compartment is divided and supplied to the second compartment including three sub-compartments partitioned in parallel. A human liver cell capsule is formed in a first sub-compartment of the second compartment, a human liver cell capsule and a macrophage capsule are separately formed in a second sub-compartment, and both the human liver cells and the macrophages are collectively encapsulated or co-cultured in a third sub-compartment.

(5) Organ (Brain (Blood-Brain Barrier/Central Nervous System))-Model

The above device is also utilizable as an organ (a brain (a blood-brain barrier/a central nervous system))-model.

Pericytes are also called Rouget cells, and are present as mesodermal cells to wrap around capillary walls. It is considered that in a cranial nerve, the pericyte forms a neurovascular unit (NVU) together with a nerve cell, a brain vascular endothelial cell, and an astrocyte (a type of glial cell present in the central nervous system) to assume functions of, for example, vascular maturation and stabilization, maintenance of the brain-blood barrier, and neuroprotection and repair during ischemia.

Figure 15A:
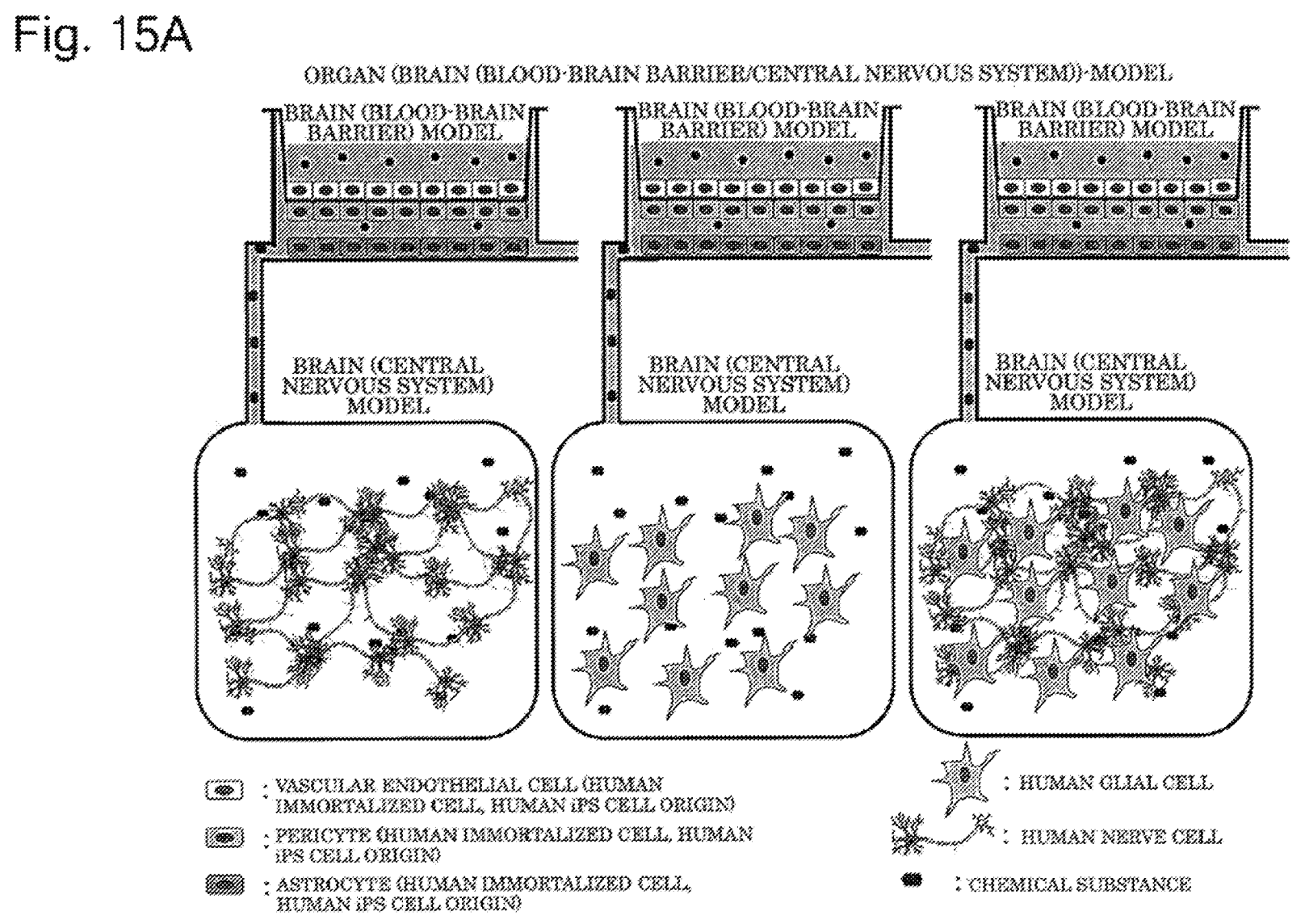

FIG. 15A and FIG. 15B show an example of the organ (the brain (the blood-brain barrier/the central nervous system))-model. Human brain vascular endothelial cells form a cell sheet on a porous membrane filter of a cell culture container. Human pericytes included in a first compartment adhere to a lower surface of the porous membrane filter of the cell culture container, to form the cell sheet. Human astrocytes adhere to a bottom surface of the first compartment, to form the cell sheet. A chemical substance is added to the first compartment. A perfusion fluid from the first compartment is supplied to a second compartment. Human nerve cells and glial cells are present in the second compartment. The nerve cells are, for example, dopamine producing cells, and the glial cells include, for example, microglia, oligodendrocyte, astrocyte, an ependymal cell, and Schwann cell. For example, when a chemical substance is added to a cell culture solution, the chemical substance passes through the vascular endothelial cells and pericytes and comes in contact with astrocytes. The chemical substance or a metabolite thereof reaches the brain (central nervous system) model in the second compartment, and hence, an influence of the substance on the nerve cells or the glial cells can be evaluated.

FIG. 15A is a configuration in which there are a plurality of independent combinations of first and second compartments. In the second compartment, nerve cells are present in a first combination (left in FIG. 15A), human glial cells are present in a second combination (middle in FIG. 15A), and both the human nerve cells and the glial cells are present and co-cultured in a third combination (right in FIG. 15A).

FIG. 15B is a configuration in which a second compartment has a plurality of sub-compartments. A perfusion fluid from a first compartment is divided and supplied to the second compartment including three sub-compartments partitioned in parallel. Nerve cells are present in a first sub-compartment, human glial cells are present in a second sub-compartment, and both the human nerve cells and the glial cells are present and co-cultured in a third sub-compartment.

(6) Organ (Intestinal Tract, Liver and Brain (Blood-Brain Barrier/Central Nervous System))-Model The above device is also utilizable as an organ (an intestinal tract, liver and brain (a blood-brain barrier/central nervous system))-model.

Figure 16:
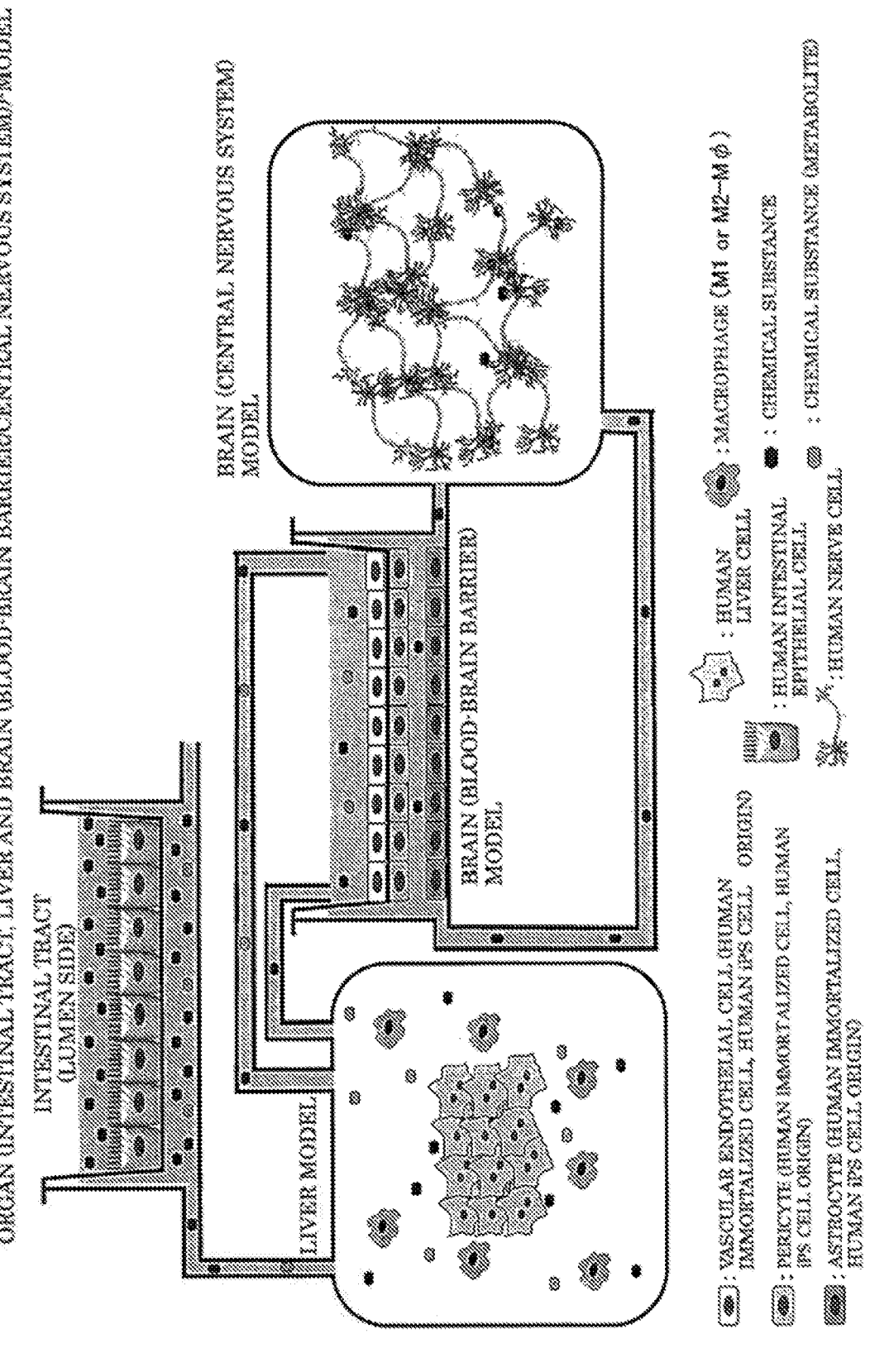
FIG. 16 is an example of an organ (an intestinal tract, liver and brain (a blood-brain barrier/central nervous system))-model.

FIG. 16 shows an example of the organ (the intestinal tract, liver and brain (the blood-brain barrier/central nervous system))-model. In this configuration, an intestinal model, a liver model, a blood-brain barrier model and a central nervous system model communicate in tandem. Effects of a chemical substance (e.g., a pharmaceutical candidate substance) on intestinal epithelial cells, liver cells, the blood-brain barrier and the central nervous system are evaluated. Human intestinal epithelial cells form a cell sheet on a porous membrane filter of a cell culture container. A chemical substance is added to a first compartment. The chemical substance enters the first compartment via the intestinal epithelial cells, and is carried by a perfusion fluid. When the chemical substance is carried through the intestinal epithelial cells, all or a part of the chemical substance can be metabolized. The perfusion fluid from the first compartment is supplied to a second compartment. The second compartment is a liver model. In the second compartment, human liver cells and macrophages (M1 or M2-Mϕ) are present. The macrophage is one type of white blood cell and a migratory phagocyte. A third compartment is a model of the blood-brain barrier. Human brain vascular endothelial cells form a cell sheet on the porous membrane filter of the cell culture container. Human pericytes contained in the third compartment adhere to a lower surface of the porous membrane filter of the cell culture container, to form the cell sheet. Human astrocytes adhere to a bottom surface of the third compartment, to form the cell sheet. A fourth compartment is a model of the central nervous system. Human nerve cells are present in the fourth compartment. The nerve cells are, for example, dopamine producing cells. An influence of the chemical substance on permeation or function of the blood-brain barrier can be evaluated.

FIG. 17 is another example of the organ (the intestinal tract, liver and brain (the blood-brain barrier/central nervous system))-model, and an example of a failure model due to intestinal flora or drug. An intestinal model, a liver model, a blood-brain barrier model and a central nervous system model communicate in tandem in the same manner as in FIG. 16. The present model is a model to evaluate effects of intestinal flora or a substance (an intestinal flora metabolite or an intestinal flora-produced substance) to be produced by the intestinal flora with growth on the intestinal tract, the liver, the blood-brain barrier or the central nervous system. The intestinal flora (*lactobacillus*, bifidobacteria, *Escherichia coli, Welsch bacillus, staphylococcus*, or the like) is added into a cell culture solution of a cell culture container. Alternatively, there may be added an intestinal flora-produced substance (a metabolite or a produced substance), or a drug that may influence the function of the intestinal tract, the liver, the blood-brain barrier or the central nervous system. The cell culture solution contains, for example, lipopolysaccharide (LPS). Human intestinal epithelial cells adhere to a bottom surface of a first compartment, to form a cell sheet. Inflammatory cytokines such as interleukins (iLs), tumor necrosis factor (TNF) α and transforming growth factor (TGF) β and a neutrophil as one type of white blood cell are present in a perfusion fluid due to an inflammatory condition. The perfusion fluid from the first compartment is supplied to a second compartment. The other configurations of the first to fourth compartments are similar to the configurations described with reference to FIG. 16.

The model of FIG. 17 is a reproduced model of a state where the intestinal tract, the liver, the blood-brain barrier or the central nervous system is impaired by the substance produced by the intestinal flora or the drug. It is possible to evaluate an influence of the substance produced by the intestinal flora or the drug on a function of the intestinal tract, the liver, the blood-brain barrier or the central nervous system.

(7) Organ (Intestinal Tract, Liver, and Kidney)-Model

The above device is also utilizable as an organ (an intestinal tract, liver, and kidney)-model.

Figure 18:
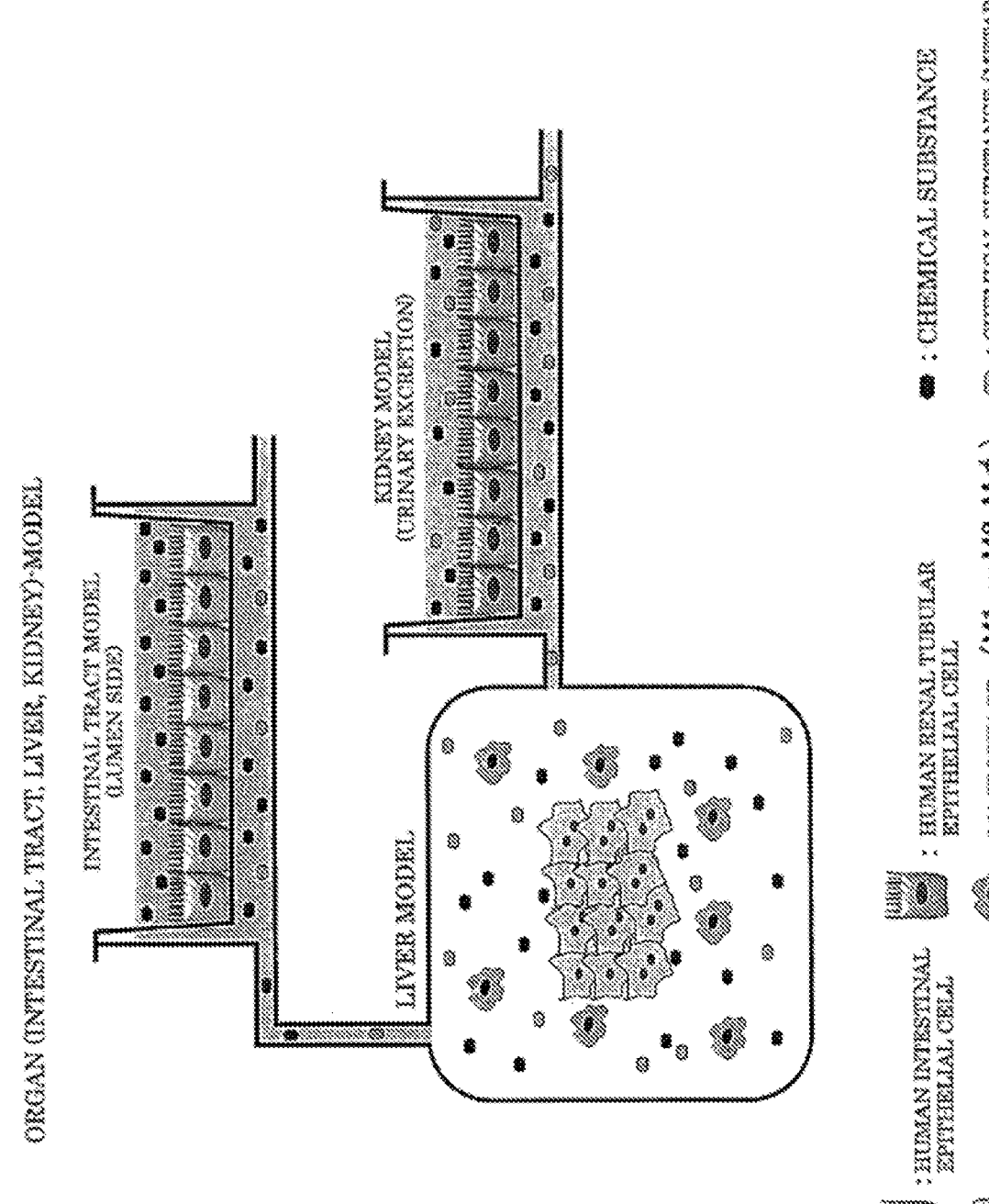
FIG. 18 is an example of an organ (an intestinal tract, liver, and kidney)-model.

FIG. 18 is an example of the organ (the intestinal tract, liver, and kidney)-model. In this configuration, an intestinal model, a liver model and a kidney model communicate in tandem. The intestinal model of a first compartment and the liver model of a second compartment are similar to the models of FIG. 16. A chemical substance is further metabolized by human liver cells of the second compartment, and carried to a third compartment by a perfusion fluid. The third compartment is a kidney model (urinary excretion). Human renal tubular epithelial cells form a cell sheet on a porous membrane filter of a cell culture container inserted in the third compartment. The chemical substance and a metabolite thereof move under the cell culture container inserted in the third compartment. During the movement, the chemical substance and a part of the metabolite thereof shift into the cell culture container via the human renal tubular epithelial cells (a tubular excretion model). Alternatively, the same chemical substance as the chemical substance added to the first compartment or a different chemical substance may be added to the cell culture container inserted in the third compartment (a tubular reabsorption model).

(8) Evaluation

Various chemical substances can be evaluated by using the above device, to provide an environment closer to a tissue or an organ of a living body. There are not any special restrictions on contents of the evaluation of the chemical substances. The contents include evaluation of any influence of the chemical substance actively or passively applied onto the living body (including a simple pass situation in the living body), for example, evaluation of in vivo pharmacokinetics of chemical substances such as the pharmaceuticals, perfumery (cosmetics), food additives, and pesticide (including metabolites of the chemical substances), evaluation of an influence (including a biological activity) on the living body, and evaluation of an influence of the living body on the chemical substance (may be generically referred to as "the evaluation of the influence on the living body" herein).

The contents non-restrictively include evaluation of the in vivo pharmacokinetics of the chemical substance, evaluation of medicinal and pharmacological effects of pharmaceuticals, evaluation of a toxicity, evaluation of effects and toxicities of the food additives on the living body, and evaluation of the toxicity of the pesticide.

The in vivo pharmacokinetics can be evaluated, for example, by checking kinetics such as a permeation amount or permeability of the administered chemical substance or the metabolite of the substance in the cells of each organ or tissue (each cell sheet or compartment of the device of the present invention).

For example, when the chemical substance is the pharmaceutical, the medicinal and pharmacological effects can be evaluated by appropriately using a known method in accordance with the pharmaceutical to be administered or a target tissue, organ or disease. A numeric value such as $EC_{50}$ or $IC_{50}$ can indicate a degree of the effect. The toxicity evaluation is necessary in safely administering a chemical substance such as the pharmaceutical in a safe administration amount for a safe administration period of time, and the toxicity can be evaluated by appropriately using a known method.

Alternatively, the contents include evaluation of an unfavorable influence (the toxicity) when the food additive, pesticide or the like is taken in the living body. This evaluation can be performed by appropriately using a known method.

EXAMPLES

Hereinafter, the present invention will be described in detail with reference to the examples, but the present invention is not limited to these examples. A person skilled in the art can easily modify or change the present invention based on the description of the present specification, and these modification and change are included in a technical scope of the present invention.

Example 1: Evaluation of First Pass Effect of Chemical Substance

In the present example, small intestine epithelial cells and liver cells were disseminated in separate compartments, and a first pass effect of a chemical substance was evaluated by using a device in which the respective compartments were connected via a flow path system. In the device described with reference to FIG. 1, Caco-2 cells were disseminated as model cells of the small intestine epithelial cells, and HepG2-CYP3A4 cells obtained by a genetic manipulation to excessively develop CYP3A4 in HepG2 cells were disseminated as model cells of the liver cells. Thus, the first pass effects (absorption and metabolism) of the chemical substance on two types of cells (the small intestine epithelial cells and the liver cells) were simultaneously evaluated.

(1) Cell

The Caco-2 cells were obtained from RIKEN BioResource Center (Ibaraki). The HepG2-CYP3A4 cells were obtained from JCRB Cell Bank (Osaka) in National Institutes of Biomedical Innovation, Corporation Health and Nutrition in National Research and Development Corporation.

(2) Cell Culture Medium

There was used Dulbecco's modified Eagle's medium (DMEM) including 10% of fatal bovine serum (FBS), 2 mmol/L of L-glutamine (L-Glu), 1% of non-essential amino acid (NEAA), 100 units/mL of penicillin G, and 100 µg/mL of streptomycin.

(3) Cell Culture a) Caco-2 Cell i) 0.4 mL of cell suspension was added to an inner side (an apical side) of a porous membrane filter at a density of 0.5 to $5 \times 105$ cells/cm$^2$ (e.g., $0.6 \times 105$ cells/cm$^2$).

ii) 0.8 mL of medium was added to an outer side (a basal side) of the porous membrane filter.

iii) The cells were cultured in a carbon dioxide gas incubator (5% of CO2 at 37° C. under humidification conditions) for about 3 weeks. An apical-side medium and a basal-side medium were appropriately changed.

Prior to use in a test, an electric resistance of a single layer film was measured by using an electric resistance measuring device. In the test, the single layer film indicating an electric resistance value of 100 to 800Ω×cm2 was used.

b) HepG2-CYP3A4 Cell i) In the device, $1.0 \times 106$ cells were disseminated.

ii) The cells were cultured in the carbon dioxide gas incubator (5% of CO2 at 37° C. under the humidification conditions).

iii) The medium was appropriately changed, and the cells were used in the test when the cells were confluent by 100% to a culture surface of the device.

(4) Preparation of Substrate Solution

Midazolam (a benzodiazepine anesthetic induction drug) was dissolved in methanol and prepared in 10 mg/mL. Furthermore, this preparation was diluted with HBSS to prepare 62.5 µg/mL of substrate solution.

(5) Perfusion Test

Each operation was carried out on a hot plate set at 40° C.

(i) HBSS (pH7.4) and a test solution were heated in a thermostatic chamber (37° C.).

(ii) Apical and basal side mediums of the plate, on which Caco-2 single layer film was prepared, were suctioned and removed.

(iii) 0.4 mL of HBSS was added to the apical side, and 0.8 mL of HBSS was added to the basal side, followed by washing. Residual HBSS was suctioned and removed.

(iv) 0.06 mL of HBSS was added to the apical side, and an insert was moved to the device.

(v) The HBSS was preliminarily perfused in the device at a flow velocity of 10 mL/hr for 10 minutes.

(vi) The HBSS was preliminarily perfused in the device at a flow velocity of 0.5 mL/hr for 5 minutes.

(vii) 240 µL of substrate solution was added to the insert, to start main perfusion.

(viii) Samples were taken from the small intestine compartment and the liver compartment every 30 minutes for 180 minutes.

(6) Quantification

By use of LC-MS-MS, midazolam and metabolites of the midazolam (1-hydroxy midazolam and 4-hydroxy midazolam) were quantified.

Result

In the small intestine compartment, successive increase of a permeation amount of midazolam permeated through the Caco-2 single layer film was recognized. Furthermore, generation of 1-hydroxy midazolam of the metabolite was confirmed (FIG. 19). Also in the liver compartment, successive increase of the permeation amount of midazolam was recognized, and accordingly, generation of 1-hydroxy midazolam and 4-hydroxy midazolam of the metabolites was confirmed (FIG. 20).

According to the above device, simultaneous use of the model cell of the intestinal epithelial cell and the model cell of the liver cell makes it possible to simultaneously and simply evaluate the absorption and metabolism of the chemical substance from the intestinal tract and the metabolism in the liver, which is impossible in a conventional method. In the present example, the model cell of the intestinal epithelial cell and the model cell of the liver cell were used. However, when a model cell of another organ is further used, the medicinal and pathological effects and toxicity can also be evaluated in addition to the absorption and metabolism. Furthermore, the present method can be utilized as an alternative method to an animal experiment, and can also contribute to animal protection.

Figure 21:
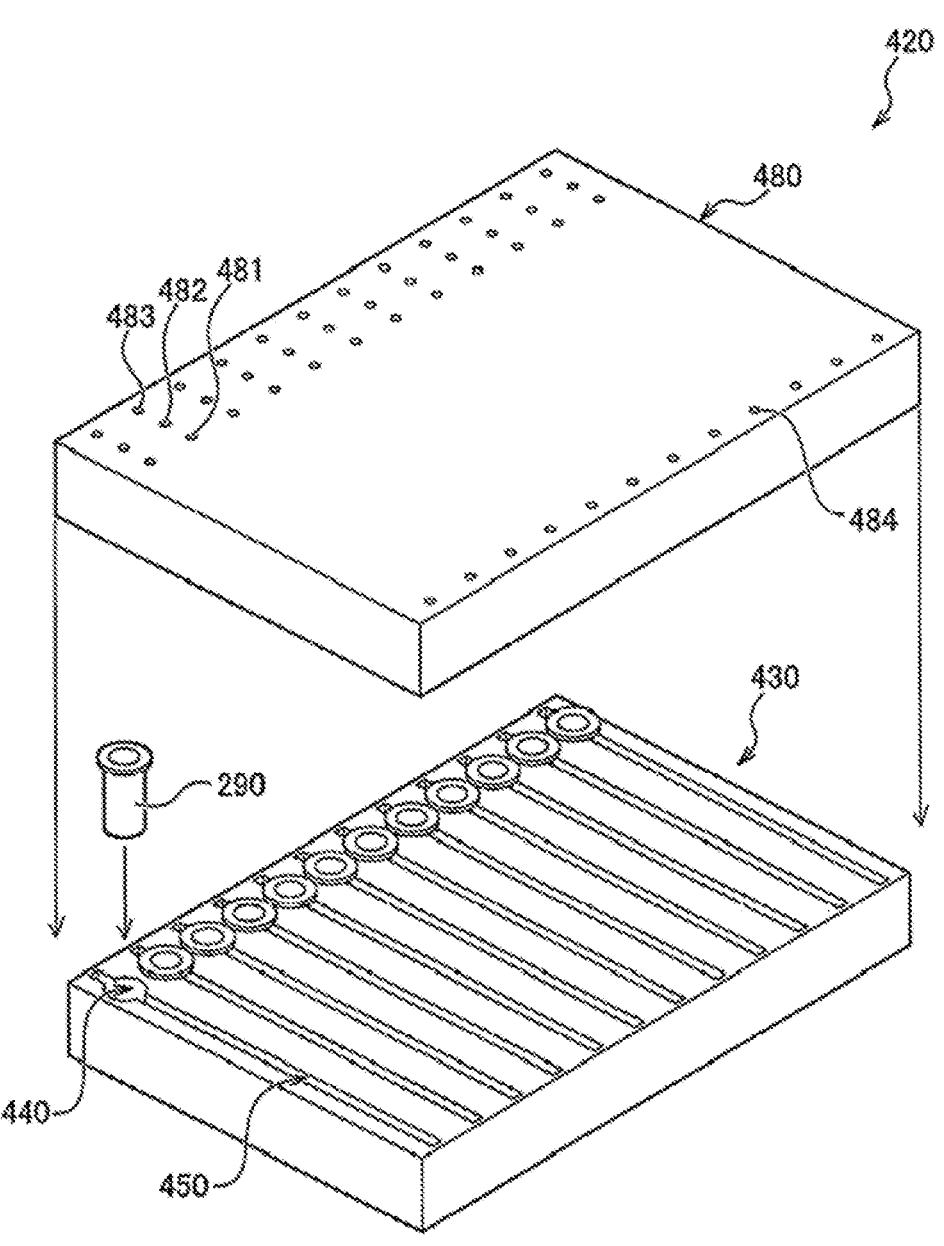
FIG. 21 is an exploded perspective view of a device for evaluation of a chemical substance according to a fifth embodiment of the present invention.
Figure 22:
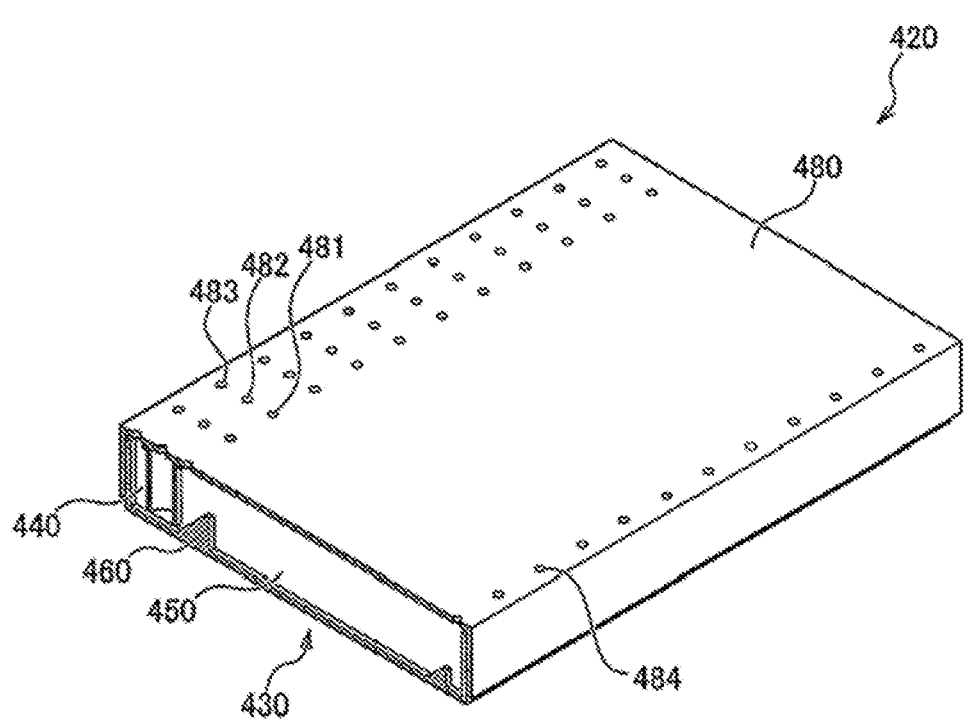
FIG. 22 is a perspective view of the device of FIG. 21 in a state where a cover is mounted to a main body.
Figure 23:
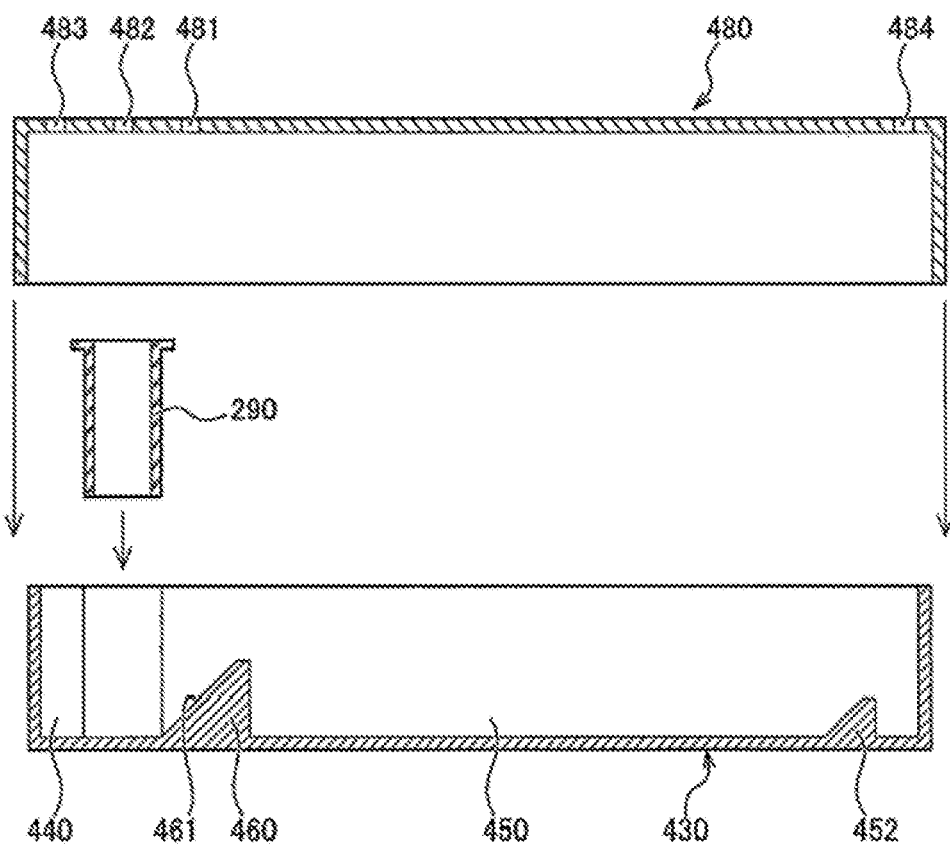
FIG. 23 is a cross-sectional view of the device of FIG. 21.
Figure 24:
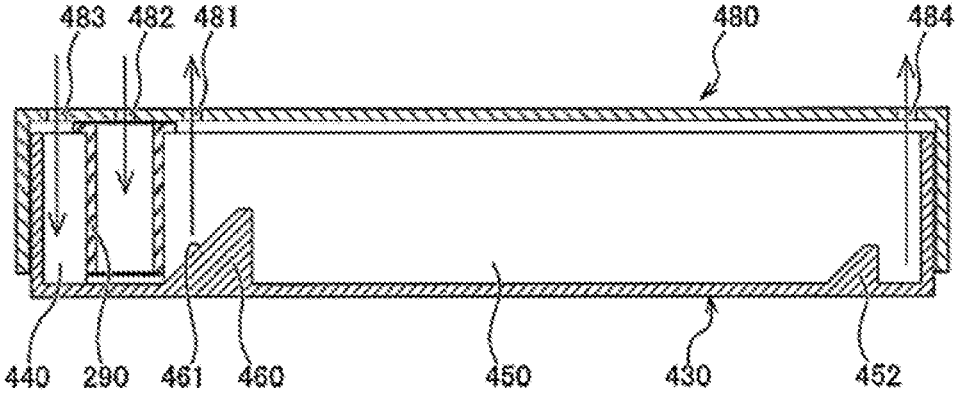
FIG. 24 is a cross-sectional view of the device of FIG. 22.

C. Another Configuration of Device:

FIG. 21 is an exploded perspective view of a device 420 for evaluation of a chemical substance according to a fifth embodiment of the present invention. FIG. 22 is a perspective view of the device 420 showing that a cover 480 is mounted to a main body 430. FIG. 23 is a cross-sectional view of FIG. 21, and FIG. 24 is a cross-sectional view of FIG. 22. Hereinafter, description will be made only as to different respects of the device 420 from the first embodiment. As shown in FIG. 21, the main body 430 of the device 420 has a substantially rectangular parallelepiped outer shape. The main body 430 includes a plurality of first compartments 440, and a plurality of second compartments 450 that communicate with the plurality of first compartments 440 in a one-to-one correspondence, respectively. Shapes of the first compartments 440 and the second compartments 450 are similar to the shapes of the second embodiment. A plurality of pairs of the first compartment 440 and the second compartment 450 (12 pairs in an example shown in the drawing) are arranged side by side in a longitudinal direction of the main body 430. An insert 290 (refer to the third embodiment) is inserted in each of the first compartments 440.

As shown in FIG. 23 and FIG. 24, the first compartment 440 and the second compartment 450 are separated by a partition wall 460 having an inclined surface 461 in the same manner as in the second embodiment. Furthermore, a wall portion 452 is formed at a downstream end of the second compartment 450 in the same manner as in the second embodiment.

The cover 480 has a size to cover the whole main body 430. In the cover 480, sampling holes 481, chemical substance throw ports 482 and inlet ports 483 are formed as many as the number of the pairs of the first compartment 440 and the second compartment 450. Functions of the sampling hole 481, the chemical substance throw port 482 and the inlet port 483 are the same as the functions of the sampling hole 81, the chemical substance throw port 82 and the inlet port 83 in the first embodiment.

In the cover 480, outlet ports 484 are further formed as many as the number of the pairs of the first compartment 440 and the second compartment 450. The outlet port 484 is formed to discharge a perfusion fluid. The outlet port 484 is disposed at a position of the main body 430 corresponding to a region on a downstream side from the wall portion 452.

In the device 420, tubes are inserted into the sampling holes 481, the chemical substance throw ports 482, the inlet ports 483 and the outlet ports 484, respectively, so that circulation of the perfusion fluid, throwing of a chemical substance and sampling of the perfusion fluid can be automatically performed. Additionally, in the single device 420, a large number of pairs of the first compartment 440 and the second compartment 450 can be compactly arranged.

Figure 25:
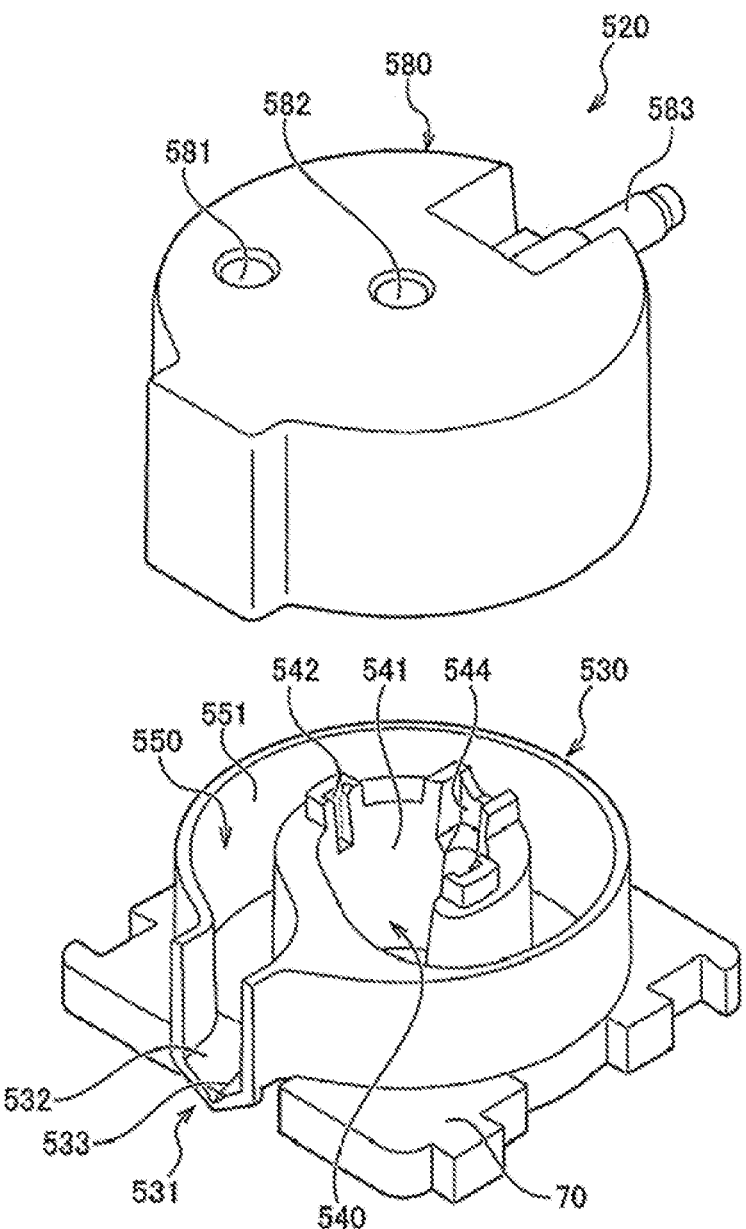
FIG. 25 is an exploded perspective view of a device for evaluation of a chemical substance according to a sixth embodiment of the present invention.
Figure 26:
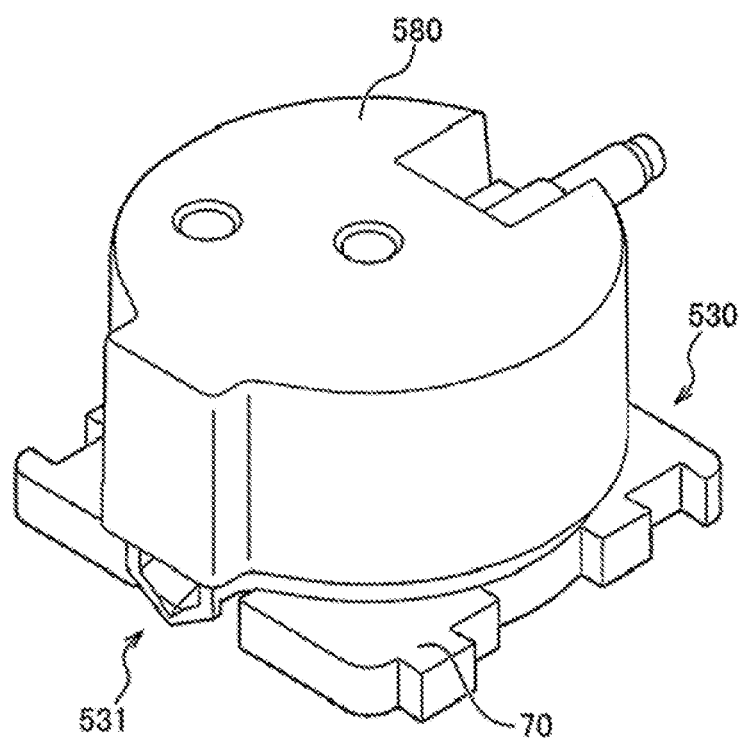
FIG. 26 is a perspective view of the device of FIG. 25 in a state where a cover is mounted to a main body.
Figure 27:
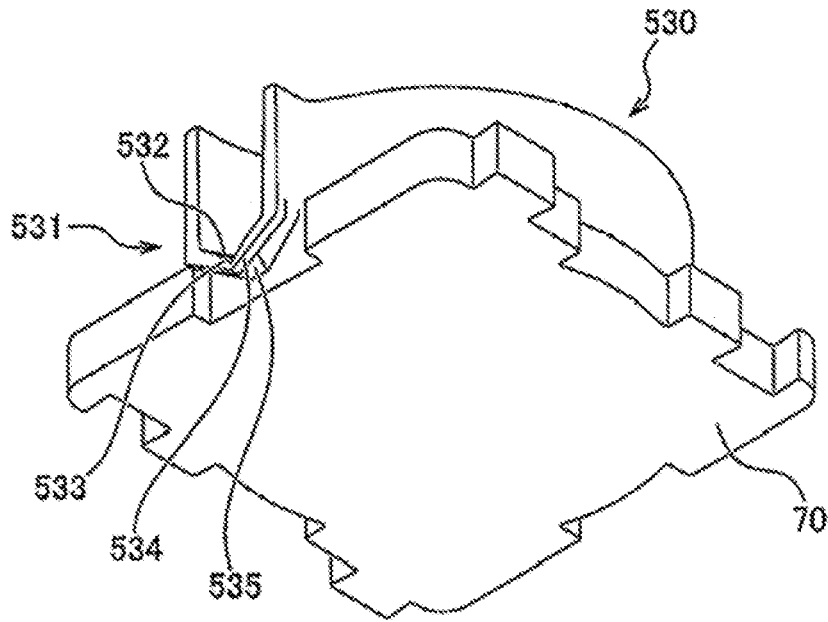
FIG. 27 is a perspective view of the main body of FIG. 25.

FIG. 25 is an exploded perspective view of a device 520 for evaluation of a chemical substance according to a sixth embodiment of the present invention. FIG. 26 is a perspective view of the device 520 showing that a cover 580 is mounted to a main body 530. FIG. 27 is a perspective view of the main body 530 of the device 520. Hereinafter, description will be made only as to different respects of the device 520 from the first embodiment. As shown in FIG. 25, the cover 580 of the device 520 has a sampling hole 581 and a chemical substance throw port 582 in the same manner as in the first embodiment. An inlet port 583 extends from a side of the cover 580 through the cover 580. The main body 530 of the device 520 includes a first compartment 540 and a second compartment 550 formed by wall portions 541 and 551 in the same manner as in the first embodiment. Further in the wall portion 541, a slit 542 is formed in the same manner as in the first embodiment. A cutout portion 544 is formed in the wall portion 541. A position of the cutout portion 544 is set so that an inner passage of the inlet port 583 opens right above the cutout portion 544.

As shown in FIG. 25, a discharge port 531 of the second compartment 550 is open toward the side (in a horizontal direction). The discharge port 531 includes an inner bottom surface 532. The inner bottom surface 532 is formed in a V-shape. Consequently, a V-shaped groove 533 is formed in the inner bottom surface 532. According to such a configuration, a discharge region of a perfusion fluid discharged from the discharge port 531 can be limited to a vicinity of a bottom portion of the V-shaped groove 533.

As shown in FIG. 27, the discharge port 531 includes an outer bottom surface 535. The outer bottom surface 535 projects downward from an outer edge portion 534 located on a downstream side of the discharge port 531 (i.e., located on an lowermost stream side). According to such a configuration, the perfusion fluid discharged from the discharge port 531 can be inhibited from flowing along the outer bottom surface 535 and entering the second compartment 550 (toward a center side of the main body 530).

Figure 28:
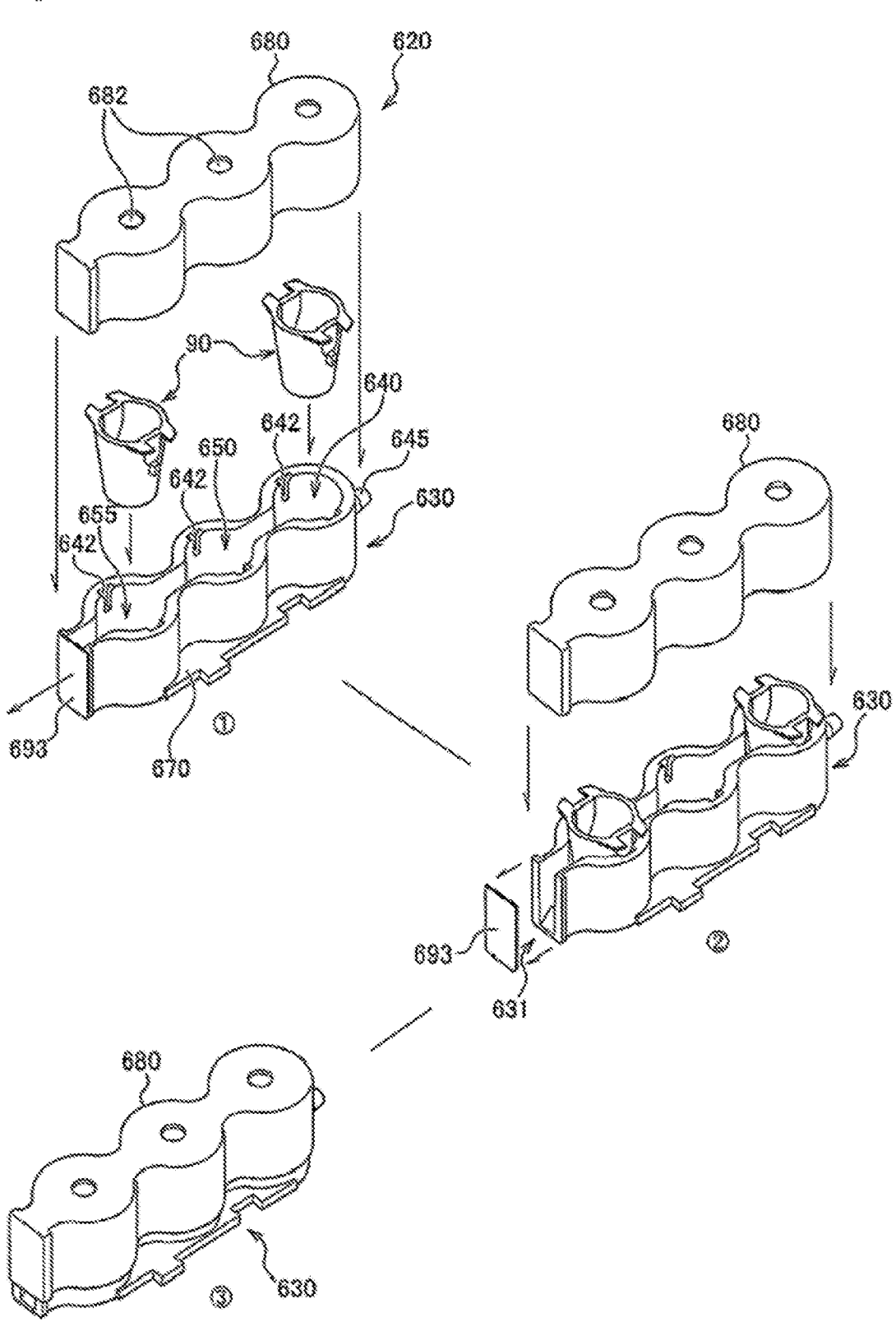
FIG. 28 is a perspective view of a device for evaluation of a chemical substance according to a seventh embodiment of the present invention.
Figure 29:
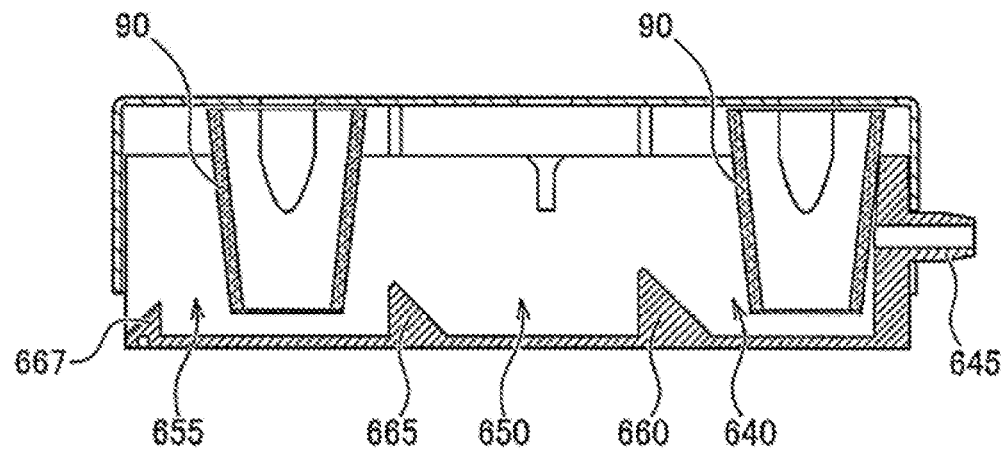
FIG. 29 is a cross-sectional view of the device of FIG. 28.

FIG. 28 is a perspective view of a device 620 for evaluation of a chemical substance according to a seventh embodiment of the present invention, showing a procedure of assembling the device 620. FIG. 29 is a cross-sectional view of the device 620. As shown in FIG. 28, a main body 630 of the device 620 includes three compartments 640, 650 and 655 that communicate in series, and a base 670. As shown in FIG. 29, the compartments 640, 650 and 655 are separated by partition walls 660 and 665. In a wall portion forming the main body 630, slits 642 to support inserts 90 are formed for the respective compartments 640, 650 and 655, respectively. An inlet port 645 is connected to the uppermost stream side compartment 640 among the compartments 640, 650 and 655. A wall portion 667 is formed in the lowermost stream side compartment 655 among the compartments 640, 650 and 655, and an outlet 631 is formed on a downstream side of the wall portion. A seal 693 may be attached to the outlet 631.

A cover 680 has a shape that follows the main body 630, and has a size that covers the compartments 640, 650 and 655. In the cover 680, chemical substance throw ports 682 are formed at positions corresponding to the respective compartments 640, 650 and 655. In addition to or in place of the chemical substance throw ports 682, sampling holes may be formed.

According to the device 620, the inserts 90 are inserted in an arbitrary number of the compartments at arbitrary positions (the compartments 640 and 655 in the shown example) among the three compartments 640, 650 and 655, so that a desired evaluation object environment can be modelled. Furthermore, when the insertion position of the insert 90 is changed, the evaluation object environment can be easily changed. Consequently, the device has an excellent versatility. The number of the compartments is not limited to three, and may be the arbitrary number of two or more.

In the above described use mode of the device, dietary fibers may be added to a liquid in the compartment. Then, the liquid to which the dietary fibers are added in the compartment may be stirred. Consequently, cells in the compartment can be stimulated by the dietary fibers.

Figure 30:
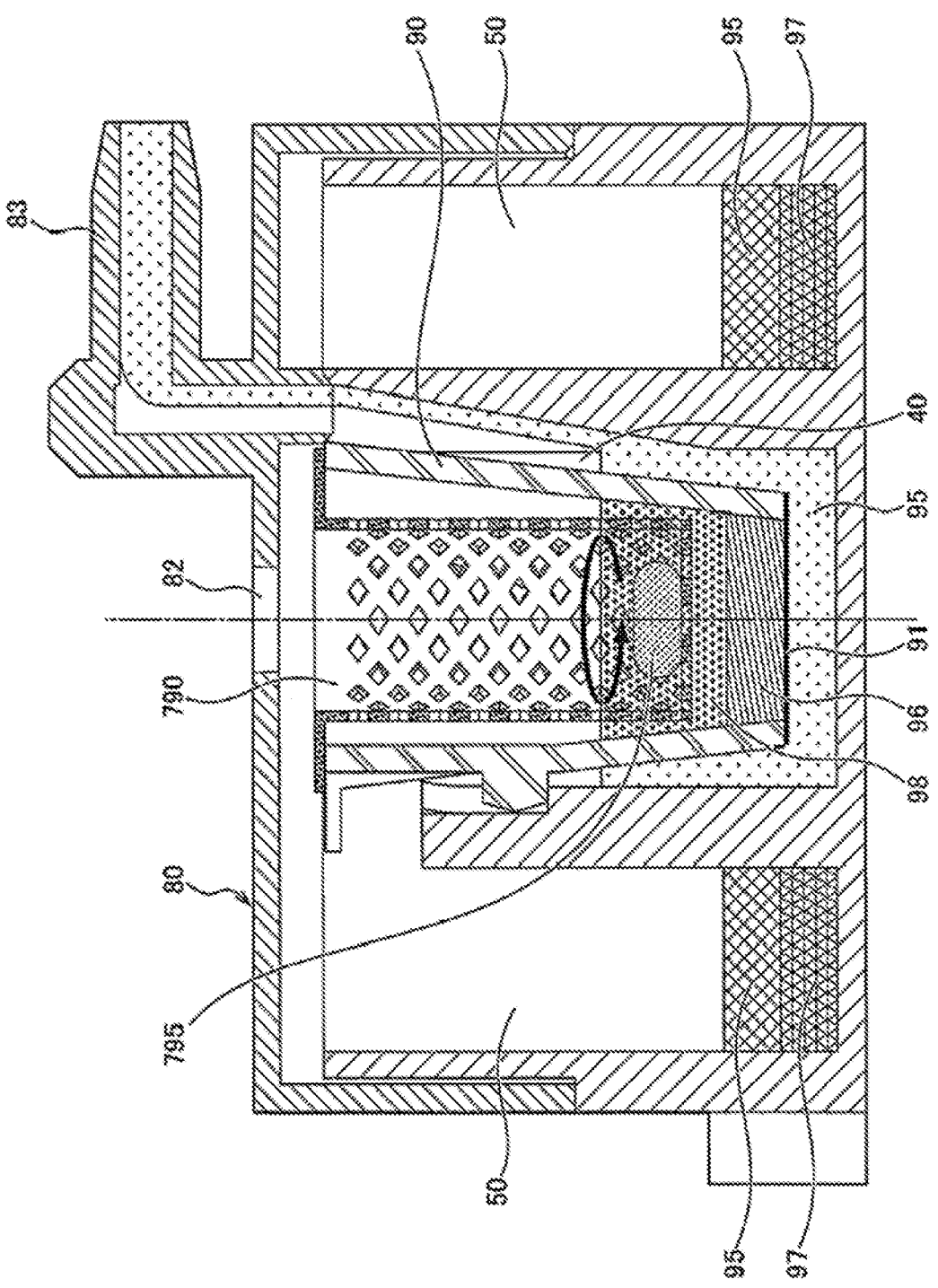
FIG. 30 is a cross-sectional view showing a behavior of stirring a content of an insert.
Figure 31:
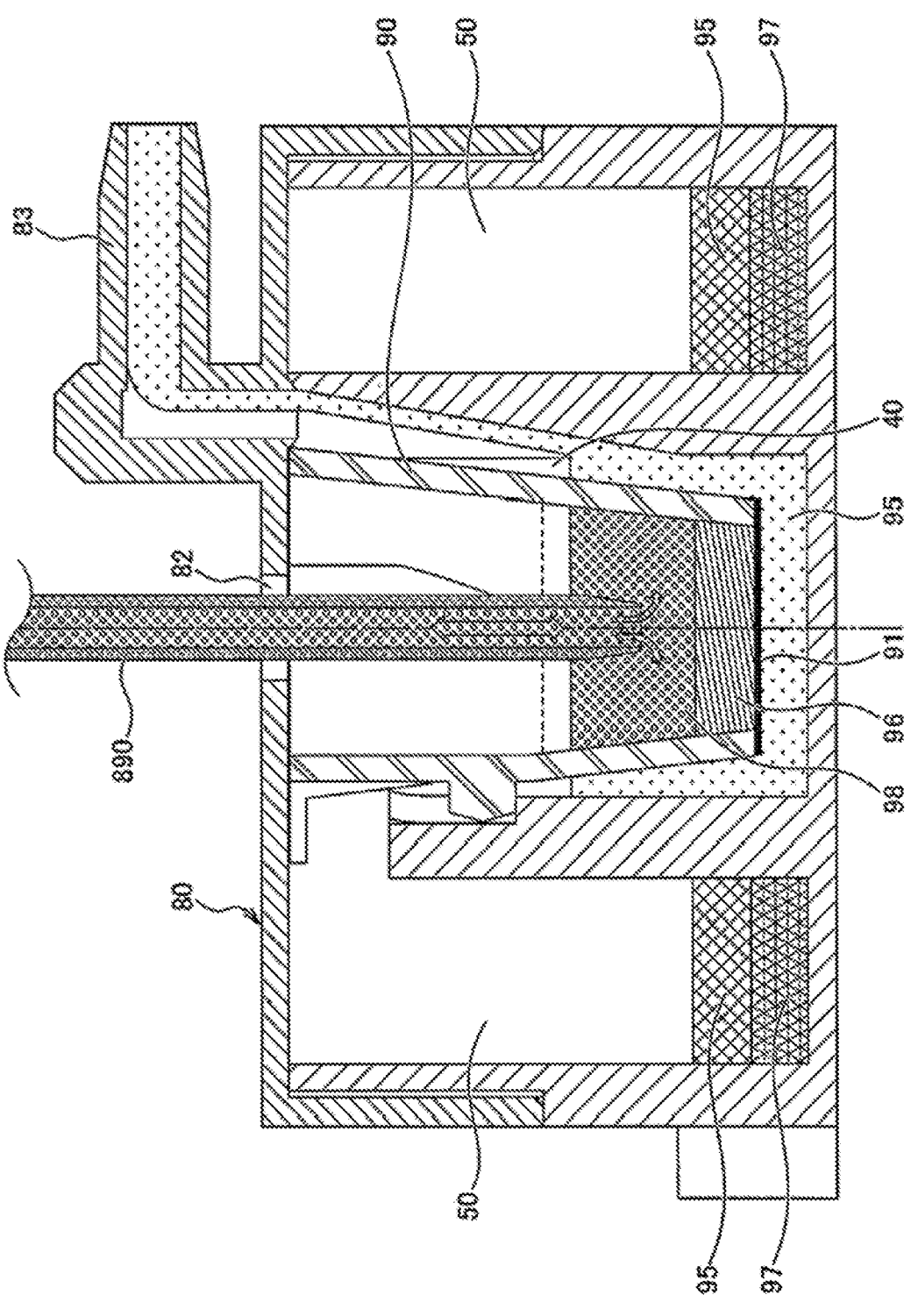
FIG. 31 is a cross-sectional view showing a behavior of stirring the content of the insert.

FIG. 30 and FIG. 31 are cross-sectional views showing a behavior of stirring a content of an insert 90 disposed in a first compartment 40. In FIG. 30 and FIG. 31, the device 20 of the first embodiment is exemplarily used. Dietary fibers are beforehand added to a medium solution 98. In FIG. 30, a container 790 having a large number of pore portions (e.g., may be meshes) is disposed in the insert 90. A rotor 795 is inserted in the container 790. In this example, the rotor 795 is rotated in the container 790 by a stirrer (not shown), so that the medium solution 98 can be stirred. In FIG. 31, a syringe 890 is used in place of the container 790 and the rotor 795. The syringe 890 is inserted via a chemical substance throw port 82. When an operation of suctioning the medium solution 98 and then returning (discharging) the solution with the syringe 890 is repeated, the medium solution 98 can be stirred.

According to various embodiments of the present invention described above, the device includes a plurality of regions (a plurality of compartments), and a communicating portion (a flow path) is formed so that the respective regions can communicate in a liquid phase (a liquid). In each of these regions, cells can be cultured. In the cell culture of each region, a single cell type may be cultured, or a plurality of types of cells may be co-cultured. Each region may be subjected to a surface treatment (surface hydrophilization, cell adhesion factor coating, or the like) so that the cell culture is possible. The type of surface treatment may be the same or different among the respective regions. Each region or a part of the communicating portion is not permeable to the cells and is permeable to a liquid factor. The region that is not permeable to the cells and is permeable to the liquid factor can be used as a cell culture surface (a cell adhesive surface).

Furthermore, flow of the liquid in one direction is formed in the communicating portion. The flow of the liquid may be generated by gravity (a gradient for this purpose may be formed), or may be generated by a liquid sending device. The flow of the liquid may be circulatory. It is preferable that the liquid is a culture fluid.

According to the above described device, a plurality of types of cells can be simultaneously and separately cultured in the same culture system. Furthermore, the cells can be disseminated in each compartment so that the plurality of types of cells are arranged in an order of involvement of the living body in the flow of the substance. For example, the cells may be disseminated in the respective compartments in an order of the intestinal cell and the liver cell, an order of the blood-brain barrier and the nerve cell, and an order of the liver cell and the ureteral cell as seen from an upstream side in a liquid flowing direction. Furthermore, in these combinations, a region of vascular endothelial cells can be provided in a middle.

The embodiments of the present invention have been described. The above embodiments are described to facilitate understanding of the present invention, and do not restrict the present invention. The present invention can be changed or improved without departing from the gist of the invention, and the present invention includes equivalents. Furthermore, any combination or omission of the respective components described in the claims and description is possible in a range in which at least parts of the above described problems can be solved or in a range in which at least parts of effects can be produced.

INDUSTRIAL APPLICABILITY

According to a device and a method using the device of embodiments of the present invention, it is possible to accurately evaluate, in vitro, an influence of a chemical substance on a living body, for example, in vivo pharmacokinetics, an effect, and a toxicity. The device and the method are useful for study of, for example, chemical substance absorption, excretion, metabolism, safety, pharmacological actions, and formulation (DDS). Furthermore, in addition to pharmaceuticals, for example, cosmetics experimented by using animal experiments cannot be sold in some areas or countries (e.g., European countries). Furthermore, as to pesticides and food additives, a toxicity experiment (a safety test) to a human cannot be performed. Also in such a case, there is a need for a model system that imitates the human or an animal. The device and method according to the embodiments of the present invention are characterized by being, for example, (1) inexpensive and simple, (2) excellent in convenience and operability, (3) high in versatility and excellent in applicability, (4) capable of evaluating the chemical substance in cells under different culture conditions, and (5) hard to generate contamination of the cells.

What is claimed is:

1. A device that provides an organ model in which multiple samples of cells are cultured for evaluations of reactions of a test chemical substance with the multiple samples of cells, comprising:

a unitary body structure with an open-top and closed-bottom channel in the unitary body structure, wherein the channel is configured to flow a supply of a perfusion fluid from an upstream side of the channel to a downstream side thereof;

a first compartment in the upstream side of the channel to have an open-top and a closed-bottom, wherein the first compartment is configured to hold inside first sample cells cultured at a cell culture height from the closed-bottom of the first compartment to form a cell sheet on a membrane inside the first compartment, further wherein the first compartment is configured to receive the test chemical substance thrown through the open-top of the first compartment upon the cultured first sample cells, further wherein the closed-bottom of the first compartment is configured to collect the test chemical substance reacted with the cultured first sample cells and passing through the membrane to join the test chemical substance collected into with the supply of the perfusion fluid, and further wherein the open-top of the first compartment is configured to provide a first passage for sampling the test chemical substance reacted with the first sample cells;

a second compartment in the downstream side of the channel to have an open-top and a closed-bottom and to receive a flow of the perfusion fluid joined with the test chemical substance collected, wherein the second compartment is configured to hold second sample cells cultured inside the second compartment, further wherein the closed-bottom of the second compartment is configured to flow the supply of the perfusion fluid, joined with the test chemical substance collected, through the second sample cells to react the test chemical substance collected with the second sample cells, and further wherein the open-top of the second compartment is configured to provide a second passage for sampling the test chemical substance reacted with both the first sample cells and the second sample cells; and a partition wall elevated from the closed bottom of the channel between the first compartment and the second compartment, wherein the partition wall is configured to have an inclined upstream surface and a vertical downstream surface, which converge to an acutely shaped edge at a top of the partition wall, the inclined upstream surface defining an inclined downstream end of the first compartment and the vertical downstream surface defining a vertical upstream end of the second compartment, further wherein the partition wall creates a reservoir of the perfusion fluid in the first compartment having a liquid surface as high as a height of the partition wall to prevent the test chemical substance thrown in the first compartment from dispersing into the reservoir of the perfusion fluid before passing through the first sample cells, and further wherein the partition wall is configured with a sloped surface to slow down the flow of the perfusion fluid from the reservoir of the perfusion fluid in the first compartment over the partition wall into the second compartment to suppress a concentration change of the test chemical substance in the perfusion fluid flowing over the partition wall into the second compartment.

2. The device according to claim 1, comprising a cover that covers the open-top of at least one of the first compartment and the second compartment.

3. The device according to claim 2, wherein the cover comprises a sampling hole through the cover.

4. The device according to claim 2, wherein the cover comprises a chemical substance throw port through the cover through which the test chemical substance is thrown into the first compartment.

5. The device according to claim 1, further comprising a cell culture container inserted in the first compartment, wherein the cell culture container comprises a closed bottom and configured to hold and culture the first sample cells inside the cell culture container at the cell culture height from the closed bottom of the first compartment, wherein the first compartment comprises a support structure to suspend the cell culture container in the first compartment so that the test chemical substance collected flows with the perfusion fluid between the closed bottom of the cell culture container and the closed bottom of the first compartment.

6. The device according to claim 5, wherein the cell culture container suspended in the first compartment is placed in part in the reservoir of the perfusion fluid.

7. The device according to claim 2, wherein the cover is a transparent member.

8. The device according to claim 1, wherein the closed bottom of each of the first compartment and the second compartment is at least in part of a transparent member.

9. The device according to claim 1, wherein the partition wall comprises a groove through the top of the partition wall from the inclined upstream surface of the partition wall through the vertical downstream surface thereof, wherein the groove flows therethrough the perfusion fluid from the first compartment into the second compartment by a capillary action to suppress pulses in the flow of the perfusion fluid flowing over the partition wall from the reservoir of the perfusion fluid in the first compartment into the second compartment.

10. The device according to claim 1, further comprising an additional fluid channel configured to circulate the perfusion fluid circulating back from the second compartment to the first compartment.

11. The device according to claim 1, wherein the second compartment is around the first compartment to at least partially surround the first compartment.

12. The device according to claim 1, wherein the second compartment is side by side with the first compartment.

13. The device according to claim 1, wherein the second compartment comprises a discharge port to discharge the perfusion fluid out from the second compartment, and the discharge port comprises a V-shaped inner bottom surface.

14. The device according to claim 13, wherein the discharge port comprises an outer edge portion on a downstream side, and an outer bottom surface of the discharge port projects from the outer edge portion.

15. The device according to claim 1, wherein the first compartment comprises an inlet port through which a continuous supply of the perfusion fluid is injected into the first compartment, wherein the liquid surface of the reservoir of the perfusion fluid in the first compartment is located below the inlet port.

* * * * *